United States Patent

Shinomura et al.

[11] Patent Number: 5,831,168
[45] Date of Patent: Nov. 3, 1998

[54] ULTRASOUND SIGNAL PROCESSOR

[75] Inventors: Ryuichi Shinomura, Higashimatsuyama; Hiroshi Masuzawa, Hachioji; Yuichi Miwa, Chofu; Kageyoshi Katakura, Tokyo, all of Japan

[73] Assignee: Hitachi, Medical Corporation, Tokyo, Japan

[21] Appl. No.: 742,182

[22] Filed: Oct. 30, 1996

Related U.S. Application Data

[60] Continuation-in-part of Ser. No. 572,877, Dec. 18, 1995, abandoned, which is a division of Ser. No. 124,555, Sep. 22, 1993, Pat. No. 5,515,727.

[30] Foreign Application Priority Data

| Sep. 22, 1992 | [JP] | Japan | 4-252576 |
| Mar. 5, 1993 | [JP] | Japan | 5-045265 |
| Oct. 30, 1995 | [JP] | Japan | 7-281437 |

[51] Int. Cl.⁶ ............................. G01N 29/06; A61B 8/00
[52] U.S. Cl. ........................ 73/602; 673/626; 600/437; 600/443; 600/444; 600/447
[58] Field of Search .................... 73/587, 591, 596, 73/598, 600, 601, 602, 618, 619, 633, 620, 625, 626, 628, 641; 128/661.01, 660.01, 661.07, 661.08; 600/437, 443, 444, 447

[56] References Cited

U.S. PATENT DOCUMENTS

| 4,632,124 | 12/1986 | Hiller et al. | 128/661.01 |
| 4,841,489 | 6/1989 | Ozaki et al. | 73/633 |
| 4,886,069 | 12/1989 | O'Donnell | 128/661.01 |
| 4,959,998 | 10/1990 | Yano | 73/626 |
| 4,983,970 | 1/1991 | O'Donnell et al. | 341/122 |
| 5,027,821 | 7/1991 | Hirama et al. | 128/661.01 |
| 5,217,017 | 6/1993 | Matsushima | 128/661.01 |
| 5,457,996 | 10/1995 | Kondo et al. | 73/625 |
| 5,462,058 | 10/1995 | Yamada et al. | 128/661.08 |
| 5,515,727 | 5/1996 | Miwa et al. | 73/602 |
| 5,591,911 | 1/1997 | Masuzawa et al. | 73/602 |

FOREIGN PATENT DOCUMENTS

| A-2-4355 | 1/1990 | Japan. |
| A-4-223289 | 8/1992 | Japan. |
| A-6-313764 | 11/1994 | Japan. |

Primary Examiner—Hezron E. Williams
Assistant Examiner—Rose M. Miller
Attorney, Agent, or Firm—Antonelli, Terry, Stout & Kraus, LLP

[57] ABSTRACT

In an ultrasound signal processor, respective received signals received at received signal processing units are sampled by a sampling clock of a frequency which is sufficiently higher than a Nyquist sampling frequency of an upper limit of a frequency band width for each of the received signals received at the received signal processing units so as to be digitized. Each of the digitized received signals is multiplied by a reference signal of a predetermined frequency to produce converted received signals in which the frequency of the digital received signal waveform is shifted, and converted signals are cumulated for a time which is longer than the sampling period. Each of the cumulated signals is processed by a clock frequency lower than the sampling clock in connection with an ultrasound beam in one direction, so that after one transmission operation of ultrasound, a plurality of ultrasound received beams are formed from the received signals received at the respective transducers.

28 Claims, 28 Drawing Sheets

FIG. 7
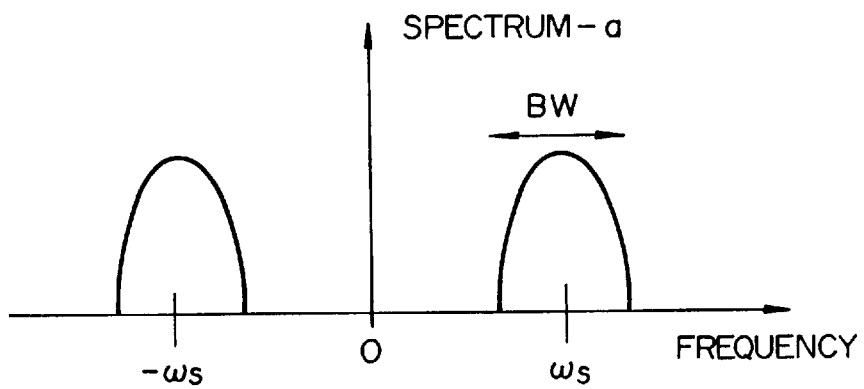
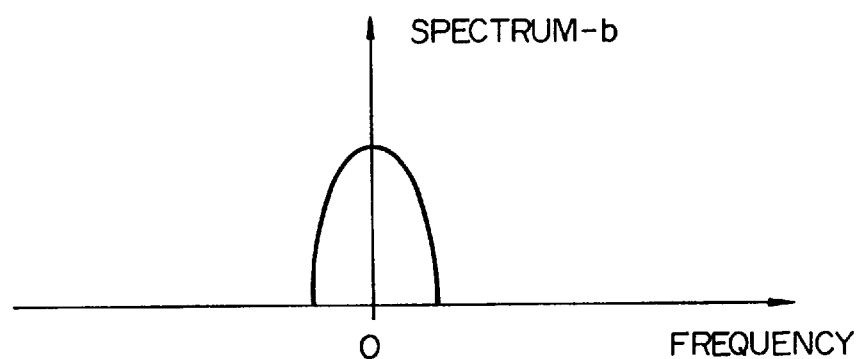
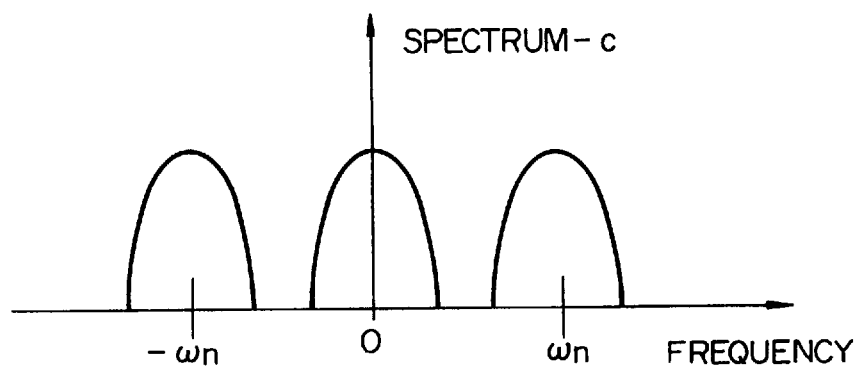
$\omega n = ADFQ / COUNT$

FIG. 9
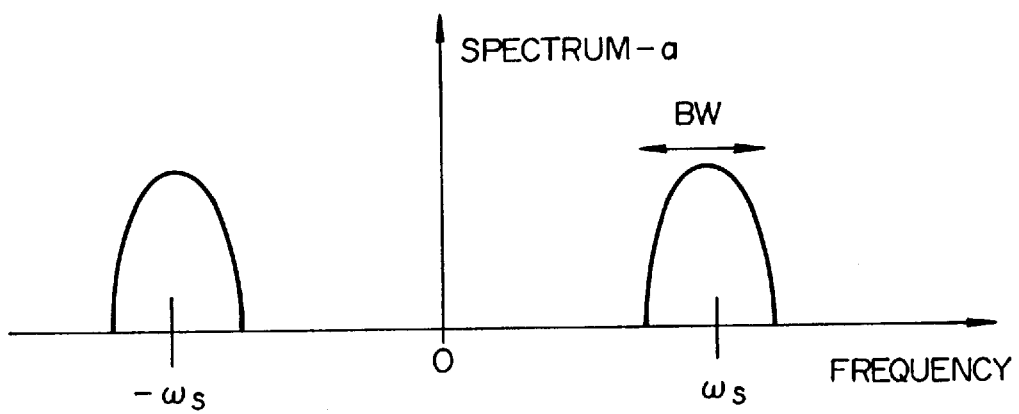
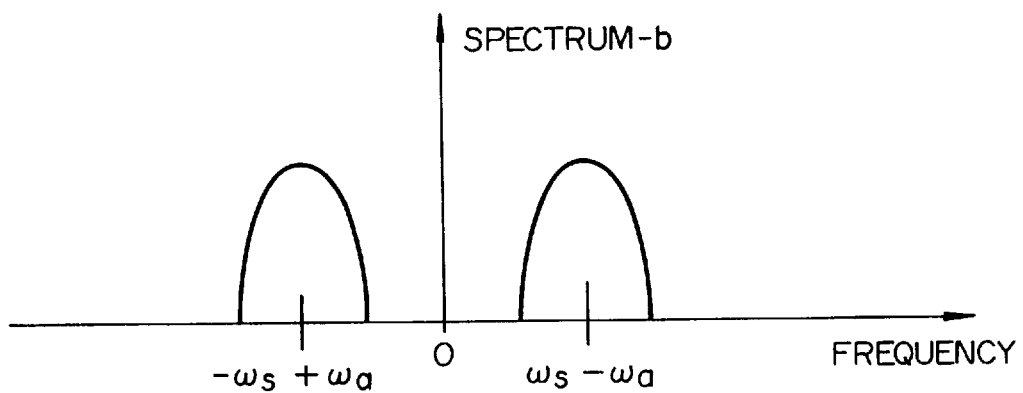

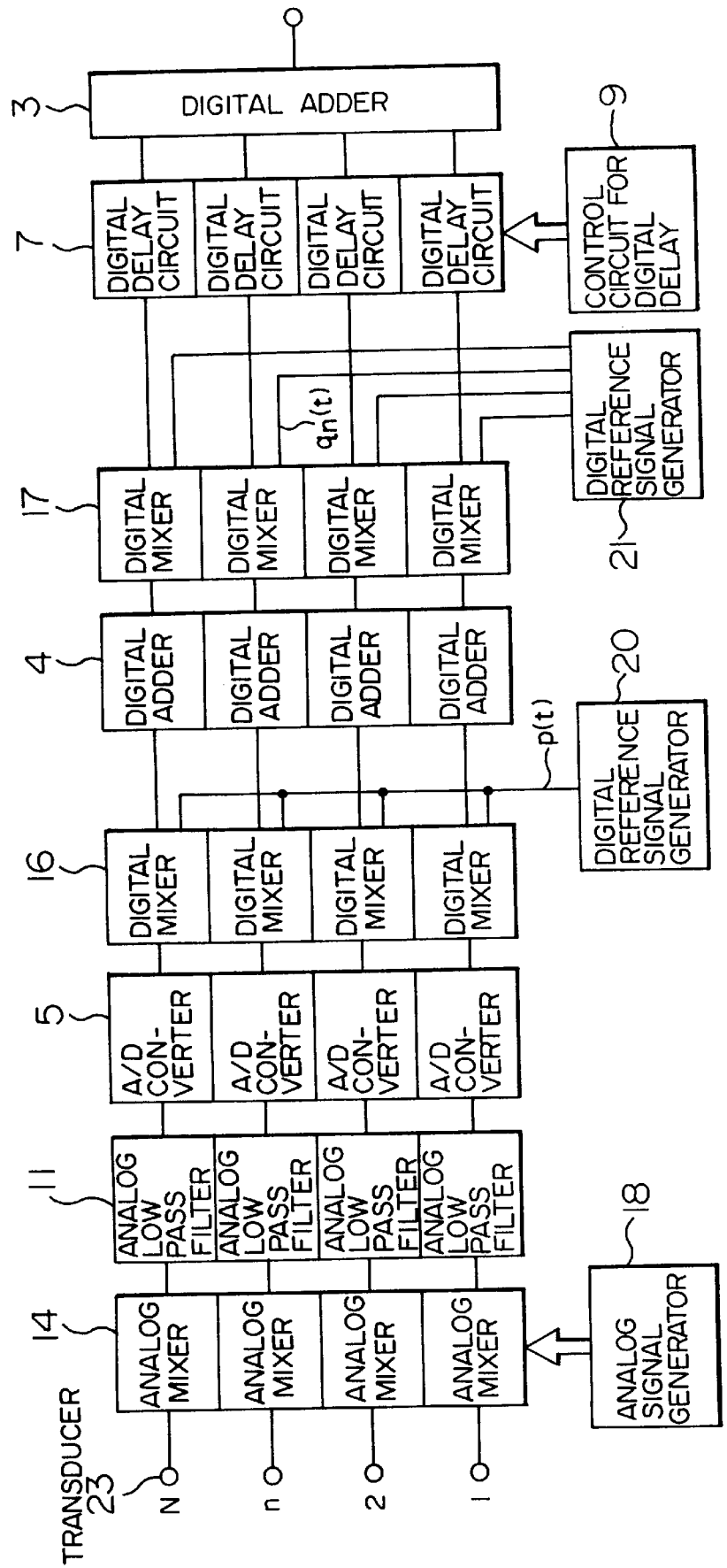
F I G. 15

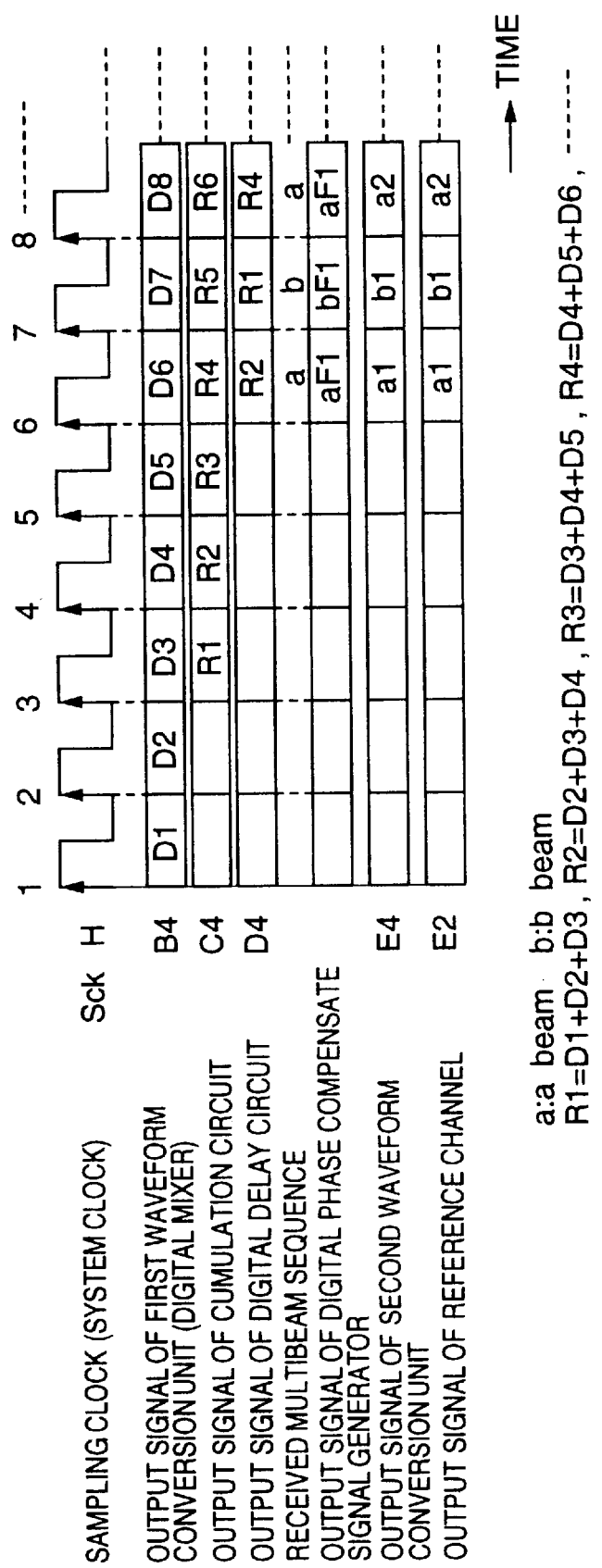

ULTRASOUND SIGNAL PROCESSOR

CROSS-REFERENCE TO RELATED APPLICATIONS

The present application is a continuation-in-part of copending U.S. patent application Ser. No. 08/572,877 filed on Dec. 18, 1995, now abandoned, under title of "ULTRASOUND SIGNAL PROCESSOR" which is a divisional application of U.S. patent application Ser. No. 08/124,555 filed on Sep. 22, 1993 issued as U.S. Pat. No. 5,515,727, the disclosure of which are hereby incorporated by reference.

BACKGROUND OF THE INVENTION

The present invention relates to signal processing either in an apparatus for performing non-destructive testing of a material object or in an ultrasound apparatus used for medical diagnosis and more particularly to an ultrasound signal processor suitable for digitization.

A conventional ultrasound receiver is comprised of analog delay circuits and adders and it radiates ultrasound to an object to be tested, then receives an echo from the object to be tested by means of a receiving element array and adjusts the delay time between receiving signals to change the direction of a receiving beam. The incident direction of the ultrasound is made to be coincident with the direction of formation of the receiving beam, and outputs of respective array receiving elements are made to be in phase and added together to thereby obtain a total output which is large.

The conventional ultrasound receiver is shown in FIG. 33. Echoes from an object to be tested are received by an array of transducers 23, respective received signals are fed to received signal processing units 44 so that a delay time difference between the received signals generated from the respective transducers may be adjusted, and output signals of the received signal processing units are added together by a digital adder 3. In this manner, a received beam 43 can be formed by a received beam forming unit 41. The received beam is electrically scanned to produce a tomogram of the object to be tested.

In order to form an optimal received beam in the course of the received beam formation, the accuracy of delay by the received signal processing unit 44 must be increased, and, to this end, various attempts have been made to eliminate disadvantages of an analog circuit (irregularities due to parts, temperature drift, saturation and the like) by changing the analog circuit to a digital circuit. However, when simple digitization of the circuit form is effected in, for example, an ultrasonic diagnostic system using ultrasound of a frequency of about 1MHz to 20MHz, high-speed ADC's (analog to digital converters) of 100MHz or more are needed. But the digitization is desired to be realized with low-speed ADC's and a method for this purpose has been proposed.

As an example, the present applicant has proposed an apparatus in JP-A-6-313764 "Ultrasound Signal Processor". In this apparatus, each received signal is digitized, a digitized received signal is multiplied by two reference signals each having a center frequency of the received signal and being 90° out of phase from each other so that the received signal may be converted into a complex signal and a low frequency component of the complex signal may be taken out, and low frequency components corresponding to signals generated from adjacent ones of the elements (transducers) are compensated for a phase difference therebetween by phase rotation and are then subjected to time delay.

JP-A-4-223289 (Japanese Patent Application corresponding to U.S. Pat. No. 4,983,970) discloses a method in which each received signal is digitized, the digitized received signal is multiplied by two reference signals each having a center frequency of the received signal and being 90° out of phase from each other so that the received signal may be converted into a complex signal and a low frequency component of the complex signal may be taken out, and low frequency components corresponding to signals generated from adjacent ones of the elements are delayed in time difference therebetween by time delay and are subjected to phase rotation.

Japanese Patent Application JP-A-2-4355 corresponding to U.S. Pat. No. 4,886,069) discloses a method for formation of a so-called received multibeam in which received signals are digitized by a plurality of ADC's arranged in parallel, the digitized signals are converted into low frequency signals by means of mixers, and the low frequency signals are applied with different phases by means of a plurality of phase rotation circuits arranged in parallel, respectively, to simultaneously form received beams in different directions. To explain the formation of received multibeam, a transmitted beam 42 is formed in a certain direction and a received multibeam is formed including received beams 43a and 43b which are formed simultaneously in different directions a and b, as shown in FIG. 34. The number of received beams of a received multibeam is not limited to two.

Receiving signals from an object other than the target, which are received by the respective array receiving elements, are out of phase from each other and consequently cancelled out to thereby produce a total output which is suppressed. Since signals received by a plurality of receiving elements are made to be in phase and added together in this manner to improve resolution, accuracy of the delay time of analog delay circuits must be increased, giving rise to problems of including a complicated apparatus configuration and high cost. Accordingly, an apparatus has been proposed which simplifies the apparatus configuration and which is mainly constructed of analog circuits which are not required to have high delay time accuracy. This type of apparatus is based on ultrasound beamforming or so-called beat-down in which the center frequency of a receiving signal is shifted and delayed and thereafter subjected to adding processing. More specifically, in the beamformer of ultrasound signals, a signal from an ultrasound receiving element is mixed with a reference signal, precisely controlled with respect to time, so as to be converted into a low frequency signal, wherein the low frequency signal component is delayed by means of a delay circuit. Signals from the respective elements which are thus produced are finally added together. A configuration using this method is shown in FIG. 2.

In FIG. 2, reference numeral 23 designates a transducer of ultrasound, 14 denotes an analog mixer, 6 indicates an analog delay circuit whose delay time is settable, 2 represents an analog adder, 18 designates an analog reference signal generator, and 8 denotes a control circuit for analog delay. Where t represents time, a transmitting signal s(t) having a center frequency $\omega_s$ can be approximated by $$S(t)=A_o(t)\{exp(j\omega_s t)+exp(-j\omega_s t)\} \quad (1)$$

wherein $A_o(t)$ indicates an envelope form of the transmitting signal and j is an imaginary unit. A receiving signal $f_n(t)$ of a targeted echo signal generated from this transmitting signal and received by an n-th array receiving element is given by $$f_n(t) = k_n s(t - \tau_n) \quad (2)$$
$$= k_n A_0(t - \tau_n)\{\exp(j\omega_s(t - \tau_n)) + \exp(-j\omega_s(t - \tau_n))\}$$
$$= A_n(t - \tau_n)[\exp\{j\omega_s(t - \tau_n)\} + \exp\{-j\omega_s(t - \tau_n)\}]$$
$$= A_n(t - \tau_n)[\exp\{j(\omega_s t - \phi_n)\} + \exp\{-j(\omega_s t - \phi_n)\}]$$

where $\tau_n$ is propagation time of the ultrasound. Here $A_n = k_n A_o$ and $k_n$ is a coefficient determined by a propagation distance of the echo. Multiplication of this signal by a reference signal $h_n(t)$ generated from the analog reference signal generator 18 is carried out by the analog mixer 14. For simplification, it is now assumed that $h_n(t)$ is a signal having the same frequency as a carrier of the receiving signal, and $h_n(t)$ is given by $$h_n(t) = \exp\{-j(\omega_s t - \phi_n)\} \quad (3)$$

when a phase term $\phi_n$ is taken into consideration. A multiplication result $g_n(t)$ is $$g_n(t) = f_n(t) h_n(t) \quad (4)$$
$$= A_n(t - \tau_n)[1 + \exp\{-2j(\omega_s t - \phi_n)\}].$$

When only a carrier component which is direct current is considered, the multiplication result is expressed by $G_n(t)$ which is $$G_n(t) = A_n(t - \tau_n) \quad (5).$$

This waveform is delayed by a time of $\tau_o - \tau_n$ by means of the analog delay circuit 6 to provide a signal $V_n(t)$ which is $$V_n(t) = G_n(t - \tau_n - (\tau_0 - \tau_n)) \quad (6)$$
$$= A_n(t - \tau_0)$$

where $\tau_o$ is a constant determined by the analog delay circuit 6. As will be seen from the above formula, signal $V_n(t)$ results from time shift of $A_n(t)$, and $A_n(t)$ is constant times as large as the envelope $A_o$ of the transmitting signal. Therefore the signal $V_n(t)$ has a common waveform whose amplitude scale depends on n. Consequently, in a final result which is obtained by adding thus processed signals by means of the analog adder 2 and which is expressed by $$Y(t) = \sum_{n=1}^{N} V_n(t), \quad (7)$$

respective signals are in phase with each other and the sum Y(t) grows greatly. On the other hand, in an echo coming from a direction other than the targeted direction, respective signals have phases which are different from φn in equation (3) and a phase term remains in equation (5). This causes interference due to the phase difference occurring during addition pursuant to equation (7), and thus the sum Y(t) damps. Based on the operational principle described above, receiving signals from the targeted direction can be selected. For example, Japanese Patent Publication No. 51068/1985 and U.S. Pat. No. 4,140,022 are relevant to this type of apparatus. The configuration shown in FIG. 2 is typically realized with analog circuits but in order to improve accuracy of beamforming and further enhance the quality of the apparatus, it may preferably be realized with digitized operation units.

Conceivably, the conventional apparatus constructed of analog circuits may be simply digitized with, for example, an apparatus constructed as shown in FIG. 3. In FIG. 3, an analog to digital converter 5 is used and the analog mixer 14, analog delay circuit 6, analog adder 2, analog reference signal generator 18 and control circuit 8 for analog delay shown in FIG. 2 are modified for digitization to provide a digital mixer 15, a digital delay circuit 7, a digital adder 3, a digital reference signal generator 19 and a control circuit 9 for digital delay, respectively, which are used in FIG. 3. In this configuration, the analog to digital (A/D) converter is required to have many bits, for example 10 bits or more, to ensure amplitude accuracy for ordinary ultrasound applications. Under the circumstances, a configuration is conceivable wherein a so-called over-sampling technique using known fast sampling and cumulation of signals in combination is applied to increase the effective number of bits. For example, in FIG. 4, a digital adder 4 for cumulation adapted to calculate the sum of a plurality of signals is arranged between the analog to digital converter 5 and digital mixer 15 shown in FIG. 3. The effect of this over-sampling technique depends on the number of cumulating operations but the ultrasound signal has a waveform as shown in FIG. 5, with the result that the time length for permitting cumulation within an amplitude change of $\Delta$ or less is limited to $T_o$ or less and a remarkable improvement in accuracy cannot be expected. In FIG. 5, A(t) represents an envelope having the same form as that of the envelope of the transmitting signal s(t) and this waveform is a typical example in the conventional ultrasonic apparatus.

In the prior art described above, when materializing a highly accurate digital beamforming processing, a problem arose in simplifying the analog to digital converter. Further, it was difficult to improve both the amplitude accuracy and the sampling frequency of the analog to digital converter in compliance with a receiving signal having a high center frequency. Further, there arose problems in dealing with a sampling frequency of the analog to digital converter that is not sufficiently higher than nearly twice the upper limit frequency of a receiving signal component.

SUMMARY OF THE INVENTION

An object of the present invention is to solve the above problems and to provide an ultrasound signal processor which can remarkably improve the accuracy of analog to digital conversion, especially for a receiving signal having a high center frequency, and can be simplified in configuration so as to be suited for cost reduction.

To accomplish the above object, a signal processor of the present invention comprises a circuit for digitizing a receiving signal, a circuit for mixing a resulting digital signal with a reference signal of a predetermined frequency to convert it into a low frequency signal, and a circuit for performing a cumulation processing of converted signals in series, whereby the cumulation processing is carried out after the frequency of the receiving signal is shifted to a lower frequency.

An ultrasound signal processor of the present invention comprises a digitizing circuit for digitizing a receiving signal, a waveform conversion circuit for converting a signal waveform by multiplying a resulting digital signal by a reference signal of a predetermined frequency, a cumulation circuit for performing a cumulation processing of converted signals in series, a delay circuit for delaying a signal subjected to the cumulation processing, and an adder circuit for adding delayed signals, whereby the cumulation processing is carried out after the frequency of the receiving signal is shifted to a lower frequency by utilizing characteristics of ultrasound signals. A plurality of groups of the waveform conversion circuits may be provided or a circuit for storing signals subjected to the cumulation processing may be provided.

To accomplish the above object, the ultrasound signal processor of the present invention further comprises a circuit for converting a receiving signal into a low frequency signal by analog-mixing the receiving signal with an analog reference signal of a predetermined frequency, and a filter circuit for passing a low frequency component of an analog-converted signal, whereby the frequency of the receiving signal is first shifted to a lower frequency through the analog signal processing, a resulting low frequency signal is digitized, the frequency of the resulting digital signals is then shifted further to a lower frequency through digital signal processing and thereafter resulting low frequency signals are subjected to a cumulation processing. An envelope of a transmitting signal can be reconstructed by limiting the number of cumulation operations during the cumulation processing of the digital converted signals and the frequency of the reference signal used during the analog waveform conversion.

In the present invention, the over-sampling technique is used for the digital processing of ultrasound signals and the cumulation processing is carried out after the frequency is shifted to a lower frequency in order that, even with a simplified configuration, the effective accuracy of analog to digital conversion can be improved greatly. Especially, by using the over-sampling technique in which an ultrasound signal having a high center frequency is shifted to a lower frequency through an analog signal processing, the frequency is further shifted to a lower frequency through a digital signal processing and thereafter a cumulation processing is carried out, the effective accuracy of analog to digital conversion can be improved greatly with a simplified configuration even for the ultrasound signal having a high center frequency.

In accordance with the present invention, by performing a cumulation processing after an ultrasound signal is shifted to a lower frequency, the over-sampling processing can act effectively to drastically improve the effective accuracy of analog to digital conversion. Through this, the configuration of the analog to digital converter in a digital type ultrasound apparatus operable at a high center frequency can be simplified, thus contributing to cost reduction. Especially, by shifting an ultrasound signal having a high center frequency to a lower frequency, digitizing a resulting low frequency signal, further shifting a resulting digital signal to a lower frequency through a digital processing, and cumulating low frequency signals, the over-sampling processing can act effectively to drastically improve the accuracy of analog to digital conversion.

Further, in order to form a received multibeam in the prior art, a plurality of received beam forming units 41 must be arranged in parallel as shown in FIG. 34. Depending on the type, a plurality of delay circuits are needed which follow a received signal processing unit.

Accordingly, the prior art need a plurality of circuits of received beam forming units for formation of a received multibeam, raising a problem that the circuit scale increases.

Another object of the present invention is to solve the above problems encountered in the prior art and provide ultrasound signal processing method and processor of the digital type suitable for formation of a received multibeam.

Still another object of the present invention is to provide an ultrasound signal processing method and processor of the digital type which can form a received multibeam without using a plurality of signal processing circuits, that is, received beam forming unit circuits for processing received signals received at transducers (elements) so as to decrease the circuit scale.

An ultrasound signal processor according to the present invention comprises an array of transducers for receiving echo signals, a digitizing circuit for setting a period of sampling in accordance with a sampling clock of a frequency which is sufficiently higher than a Nyquist sampling frequency of an upper limit frequency of a frequency band width for each of the received signals received at the transducers and sampling and digitizing each received signal, first waveform conversion units connected to each digitizing circuit in one to one relation and operative to multiply digital received signals obtained at the digitizing circuits by a reference signal of a predetermined frequency to convert the digital received signals into complex signals and shift the frequency of the digital received signals, cumulation circuits connected to each first waveform conversion unit in one to one relation and operative to cumulate received signals converted by the first waveform conversion unit for a time which is sufficiently longer than the sampling period so as to produce cumulated signals, multi-direction delay units connected to the cumulation circuits in one to one relation and operative to process the cumulated signals at a clock frequency which is lower than the sampling clock in connection with an ultrasound beam in one direction so as to form received ultrasound beams in a plurality of directions through a time sharing process, and a digital adder for adding output signals of the respective multi-direction delay units, whereby a processing is carried out in which after one transmission operation of ultrasound, a plurality of ultrasound received beams are formed from the received signal generated from each of the transducers.

The aforementioned ultrasound signal processor further comprises a control unit for a received beam former having a unit for detecting a phase error between output signals of multi-direction delay units corresponding to adjacent ones of the transducers in one to one relation and being operative to control each multi-direction delay unit so as to form a received ultrasound beam which makes the phase error substantially zero.

An ultrasound signal processor according to the present invention comprises an array of transducers for receiving echo signals, a digitizing circuit for setting a period of sampling in accordance with a sampling clock of a frequency which is sufficiently higher than a Nyquist sampling frequency of an upper limit frequency of a frequency band width for each of the received signals received at the transducers and sampling and digitizing the received signal, first waveform conversion units connected to each digitizing circuit in one to one relation and operative to multiply a digital received signal obtained at the digitizing circuit by two reference signals of a predetermined frequency which are 90° out of phase from each other to convert the digital received signal into a complex signal and shift the frequency of the digital received signal, digital cumulation circuits connected to each first waveform conversion unit in one to one relation and operative to cumulate received signals converted by the first waveform conversion units for a time which is sufficiently longer than the sampling period so as to produce a cumulated signal, a temporary memory connected to the cumulation circuit in one to one relation to temporarily store the cumulated signal, a control unit for temporary memory adapted to control delivery of the cumulated signal from the temporary memory, second waveform conversion units connected to the temporary memory in one to one relation and operative to apply phase rotation to the cumulated signal delivered out of the temporary memory, digital delay circuits connected to the second waveform conversion units in one to one relation and operative to apply a delay time to the output signals of the second waveform conversion units so as to compensate a propagation time difference of ultrasound due to a difference in distance between a target focus position and each of the transducers, a digital adder for adding output signals of the respective digital delay circuits, and a unit for converting an output signal of the digital adder into an envelope signal, whereby in order to form received ultrasound beams in a plurality of different directions in correspondence to one transmission operation of ultrasound, the temporary memory control unit controls the cumulated signal delivered out of the temporary memory to form the received ultrasound beams through a time sharing process, thereby forming ultrasound beams in the plurality of directions.

The aforementioned ultrasound signal processor further comprises a control unit for a received beam former having a unit for detecting a phase difference between output signals of digital delay circuits corresponding to adjacent ones of the transducers in one to one relation and being operative to control each temporary memory, each second waveform conversion unit and each digital delay circuit so as to form a received ultrasound beam which makes the phase error substantially zero.

Further, an ultrasound signal processor according to the present invention comprises an array of transducers for receiving echo signals, a digitizing circuit for setting a period of sampling in accordance with a sampling clock of a frequency which is sufficiently higher than a Nyquist sampling frequency of an upper limit frequency of a frequency band width for each of the received signals received at the transducers and sampling and digitizing each received signal, first waveform conversion units connected to each digitizing circuit in one to one relation and operative to multiply a digital received signal obtained at the digitizing circuit by two reference signals of a predetermined frequency which are 90° out of phase from each other to convert the digital received signal into a complex signal and shift the frequency of the digital received signal, a cumulation circuit connected to each first waveform conversion unit in one to one relation and operative to cumulate received signals converted by the first waveform conversion units for a time which is sufficiently longer than the sampling period so as to produce a cumulated signal, a digital delay circuit connected to each cumulation circuit in one to one relation and operative, for the purpose of forming received ultrasound beams in a plurality of different directions in correspondence to one transmission operation of ultrasound, to compensate a propagation time difference of ultrasound due to a difference in distance between a target focus position and each of the transducers and apply to the cumulated signal a delay time for forming the received ultrasound beams in the plurality of different directions through a time sharing process, second waveform conversion units connected to each digital delay circuit in one to one relation and operative to apply phase rotation to an output signal of each digital delay circuit, a digital adder for adding output signals of the respective second waveform conversion units, and a unit for converting an output signal of the digital adder into an envelope signal, whereby a processing is carried out in which after one transmission operation of ultrasound, the plurality of ultrasound received beams are formed from the received signal received at each of the transducers.

The aforementioned ultrasound signal processor further comprises a unit for shading the amplitude of the output signal of the second waveform conversion unit, and a control unit for a received beam former having a unit for detecting a phase error between output signals of digital delay circuits corresponding to adjacent ones of the transducers in one to one relation and operative to control each second waveform conversion unit and each digital delay circuit so as to form a received ultrasound beam which makes the phase error difference substantially zero.

An example of "setting a period of sampling in accordance with a sampling clock of a frequency which is sufficiently higher than a Nyquist sampling frequency of an upper limit frequency of a frequency band width for each of the received signals" will be described below. For example, given that the center frequency of ultrasound is 5 MHz and the upper limit of the frequency band width is 7.5 MHz, the sampling clock of the sufficiently high frequency has a frequency which is sufficiently higher than a Nyquist sampling frequency of 15 MHz for the 7.5 MHz upper limit of the frequency band width and which is, for example, 25 MHz.

An example of "to cumulate received signals for a time which is sufficiently longer than the sampling period" is as follows. In connection with the above example, the aforementioned 25 MHz is equivalent to a sampling period of 40ns and therefore, on the assumption that two or more cumulation (addition) operations are carried out, the cumulation processing is effected for a time sufficiently longer than the sampling period which is here 80ns or more.

An example of "to process the cumulated signal at a clock frequency which is lower than the sampling clock in connection with one ultrasound beam" is as follows. When the received signal is processed at intervals of 40ns for forming two ultrasound beams through a time sharing process, the received signal is processed at time intervals of 80ns (corresponding to a frequency of 12.5 MHz) in the processing for formation of one ultrasound beam and the cumulated signal is processed by a clock of a frequency which is half the 25 MHZ.

An example of "the baseband signal is lowered to a frequency which is sufficiently lower than a center frequency of the first received signal" is as follows. As an example, given that the center frequency of the received signal is 5 MHz and a signal component of the upper limit of the frequency band width is 7.5 MHz, a 5 MHz component of the received signal is shifted to a lower frequency of 0 MHz and the 7.5 MHz component is shifted to a lower frequency of 2.5 MHz in a baseband signal obtained after mixing is effected using reference signals having a frequency equal to the 5 MHz center frequency, indicating that the baseband signal is lowered to a frequency which is sufficiently lower than the center frequency of the first received signal.

Thus, the present invention has an excellent advantage that an ultrasound signal processor of the digital type suitable for formation of a received multibeam, especially, an ultrasound signal processor capable of forming a received multibeam without using a plurality of received beam forming unit circuits can be realized.

BRIEF DESCRIPTION OF THE DRAWINGS

FIG. 7 is a graph for explaining the beat-down of a receiving signal in the present invention.

FIG. 9 is a graph showing how spectra of a receiving signal change due to analog mixing.

FIG. 15 is a diagram showing a configuration of an ultrasound signal processor according to a fourth embodiment of the present invention.

FIG. 35 is a time sequence chart in the eleventh embodiment.

DESCRIPTION OF THE PREFERRED EMBODIMENTS

Figure 1:
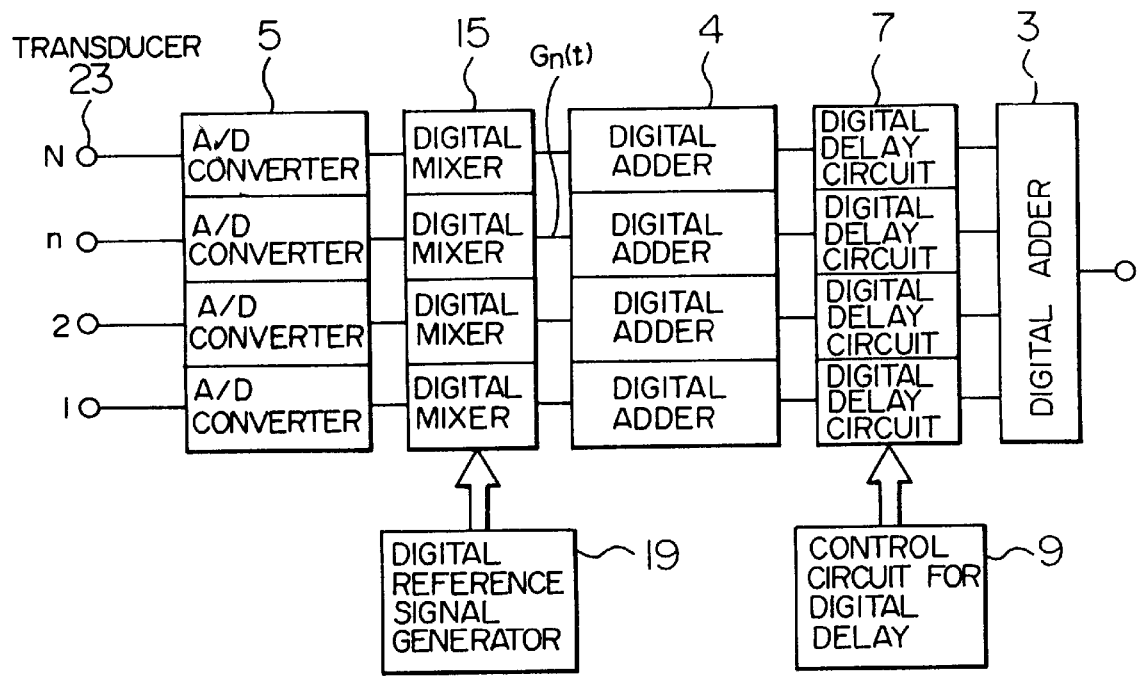
FIG. 1 is a diagram showing a configuration of an ultrasound signal processor according to a first embodiment of the present invention.
Figure 2:
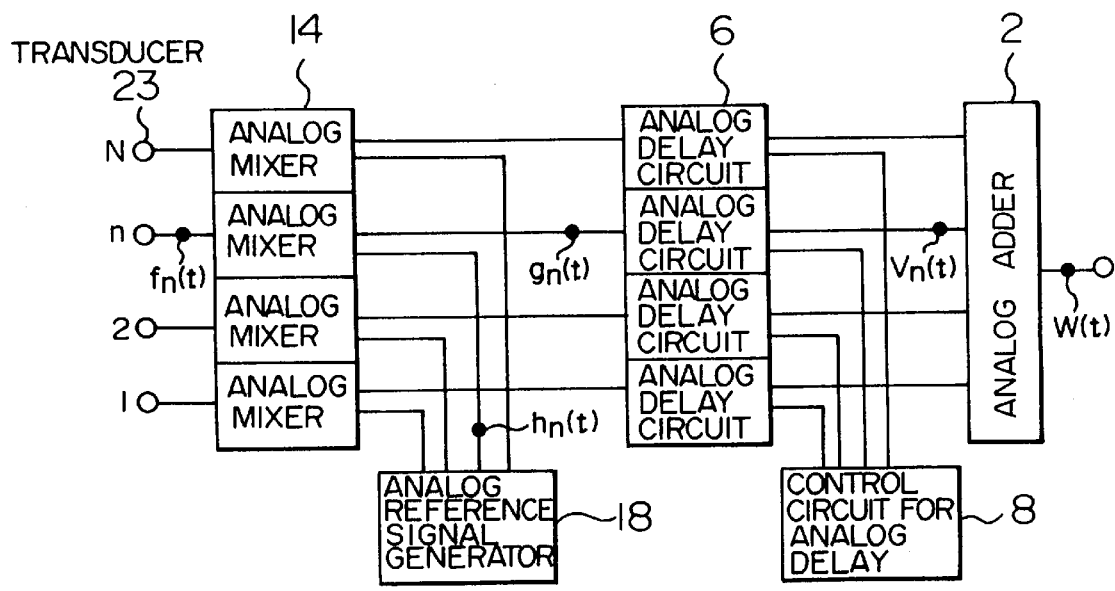
FIG. 2 is a diagram showing a configuration of a prior art analog type ultrasound signal processor to which the beat-down beamforming is applied.
Figure 3:
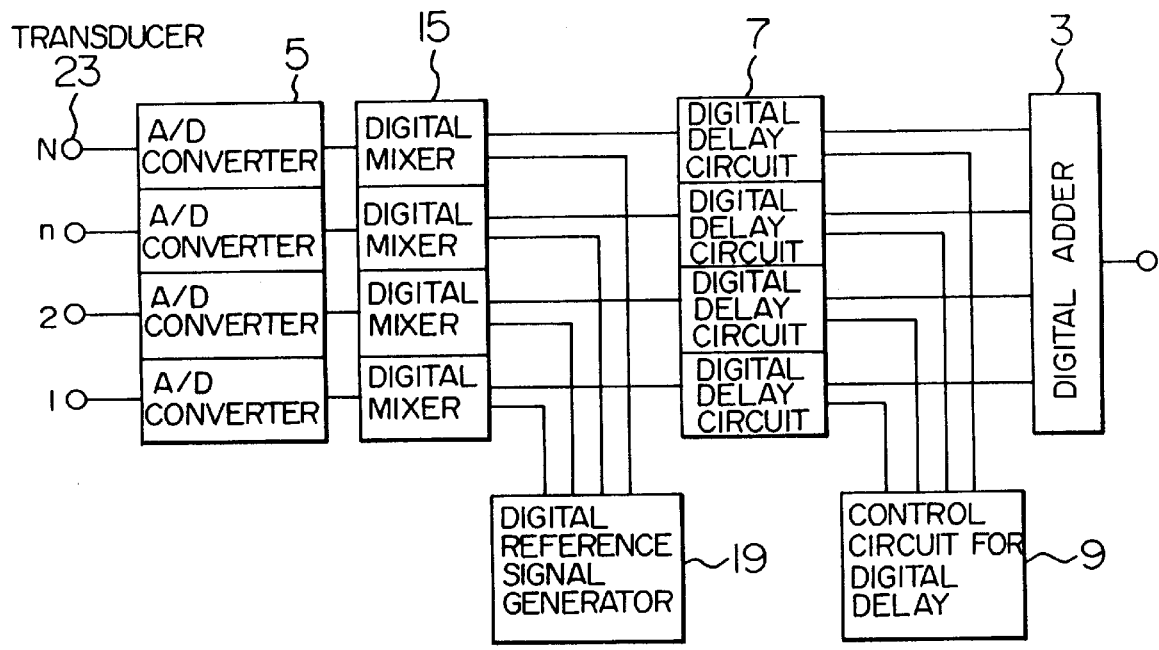
FIG. 3 is a diagram showing a configuration wherein the ultrasound signal processor of FIG. 2 is digitized.
Figure 4:
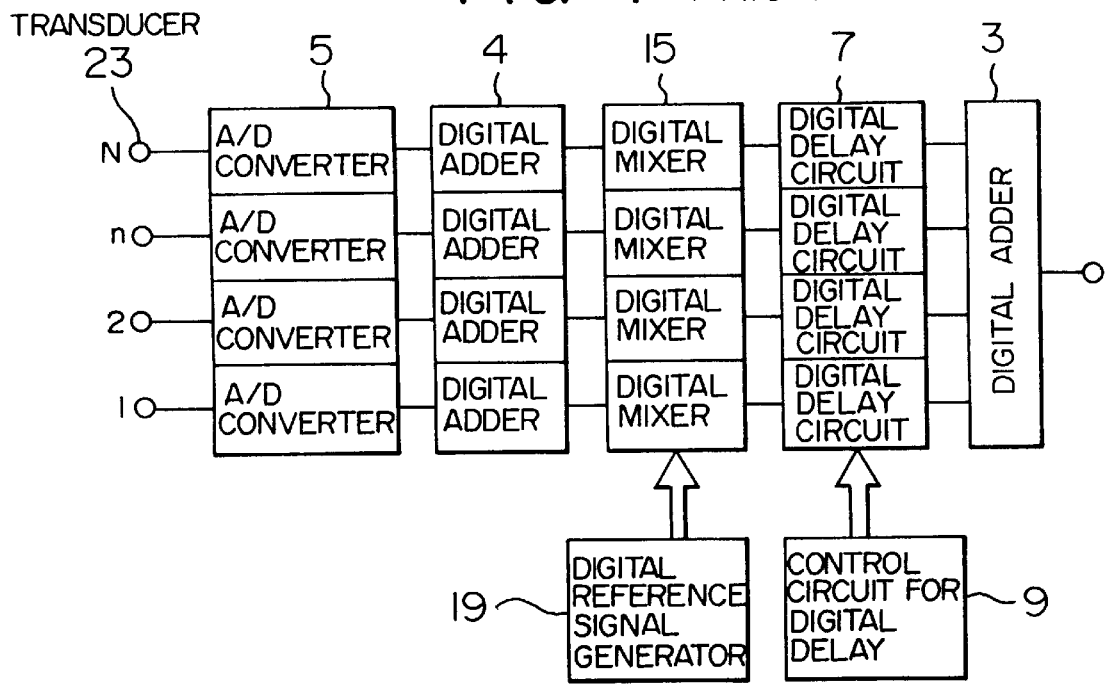
FIG. 4 is a diagram showing a configuration wherein the over-sampling technique is applied to the ultrasound receiver of FIG. 3.
Figure 5:
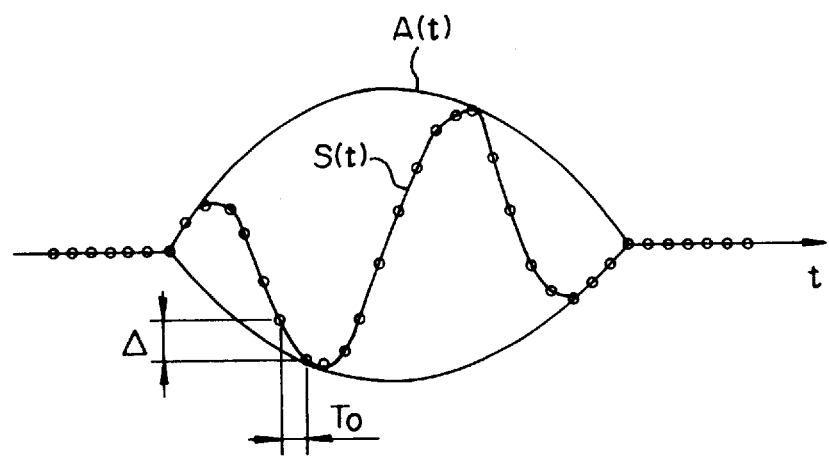
FIG. 5 is a diagram showing an ultrasound waveform obtained with the prior art ultrasound signal processor.
Figure 6:
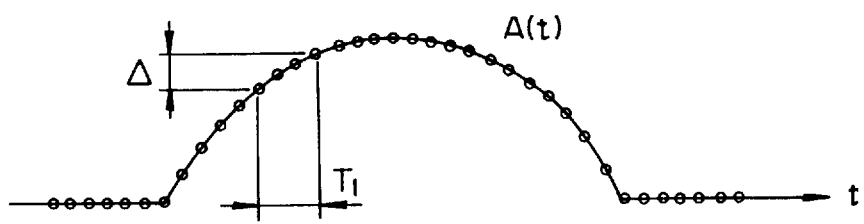
FIG. 6 is a diagram showing an ultrasound waveform obtained with the ultrasound signal processor according to the first embodiment of the present invention.

Embodiments of the present invention will now be described with reference to the accompanying drawings.
First Embodiment FIG. 1 is a diagram showing a configuration of an ultrasound signal processor for realization of accurate digital beamforming processing according to a first embodiment of the present invention. In FIG. 1, a digital adder 4 for cumulation adapted to calculate the sum of signals in series is interposed between the digital mixer 15 and digital delay circuit 7 shown in FIG. 3. In this case, signals to be cumulated are of low frequency component $G_n(t)$ delivered out of the digital mixer 15, that is, of an envelope form corresponding to $A_n(t-\tau_n)$ pursuant to equation (5). Therefore, as shown in FIG. 6, cumulation processing can proceed for a much longer time $T_l$ than $T_o$ shown in FIG. 5. The number of cumulating operations in the digital adder 4 for cumulation will be described. A spectrum as shown in FIG. 7 is an amplitude spectrum of s(t) and BW represents a band width of envelope A(t). Practically, because of sampling at the analog to digital converter, the spectrum a undergoes aliasing at a period of a sampling frequency of the analog to digital converter, but here, on the assumption that the sampling frequency of the analog to digital converter is sufficiently larger than $\omega_s$, spectrum aliasing is omitted. Since the spectrum a in FIG. 7 is subjected to multiplication by $\exp(-j\omega_s t)$ at the digital mixer 15 and to extraction of a low frequency component at the digital adder 4 for cumulation, an envelope spectrum centered at the zero frequency as shown at spectrum b in FIG. 7 develops as a spectrum of the adder output. In this phase, signal sampling frequency is reduced to (ADFQ/COUNT), where ADFQ is the sampling frequency of the analog to digital converter 5 and COUNT is the number of cumulation operations in the digital adder 4 for cumulation. Since the effect of improving S/N in the over-sampling technique becomes remarkable as the number of cumulation operations in the digital adder 4 for cumulation increases, aliasing at a period of the above (ADFQ/COUNT) cannot be neglected and there results a spectrum c as shown in FIG. 7. In order to completely reconstruct the envelope, duplication of the spectrum aliasing must be avoided and hence $$COUNT \leq (ADFQ/BW) \tag{8}$$

must stand. In this manner, a condition imposed on the number of cumulation operations is determined automatically from the band width of the envelope and the sampling frequency of the analog to digital converter. However, when improvement on S/N due to the number of cumulation operations is desired to predominate over slight overlapping of spectrum aliasing, equation (8) need not be satisfied. Returning to FIG. 1, the sampling theorem prescribes that the sampling frequency of the analog to digital converter 5 should be twice or more an upper limit frequency necessary for a frequency band of the transmitting signal s(t). On the assumption that the upper limit frequency is about 5MHz, the sampling frequency of the analog to digital converter 5 may be 10 MHz or more and the over-sampling can be effected satisfactorily by using an analog to digital converter 5 of, for example, 25MHz which is easily available at present. In addition, when the analog to digital converter 5 operates at 25MHz, the operation frequency of the digital mixer 15 is also 25MHz, thus permitting easy integration. Accordingly, the configuration exemplified in FIG. 1 is said to be very suitable for highly accurate digital beamforming processing. But when the aforementioned upper limit frequency is set to 15MHz, the analog to digital converter 5 needs a sampling frequency which is at least 30MHz and for the over-sampling, an analog to digital (A/D) converter of very high operation frequency (assumed to be 2.5 times larger than 30MHz, amounting up to 75MHz) is needed which is expensive and has high power consumption. The operating frequency of the digital mixer 15 also increases and integration is difficult to achieve. As will be seen from the above, the configuration example shown in FIG. 1 has difficulties in dealing with a high frequency ultrasound signal.

Second Embodiment

Figure 8:
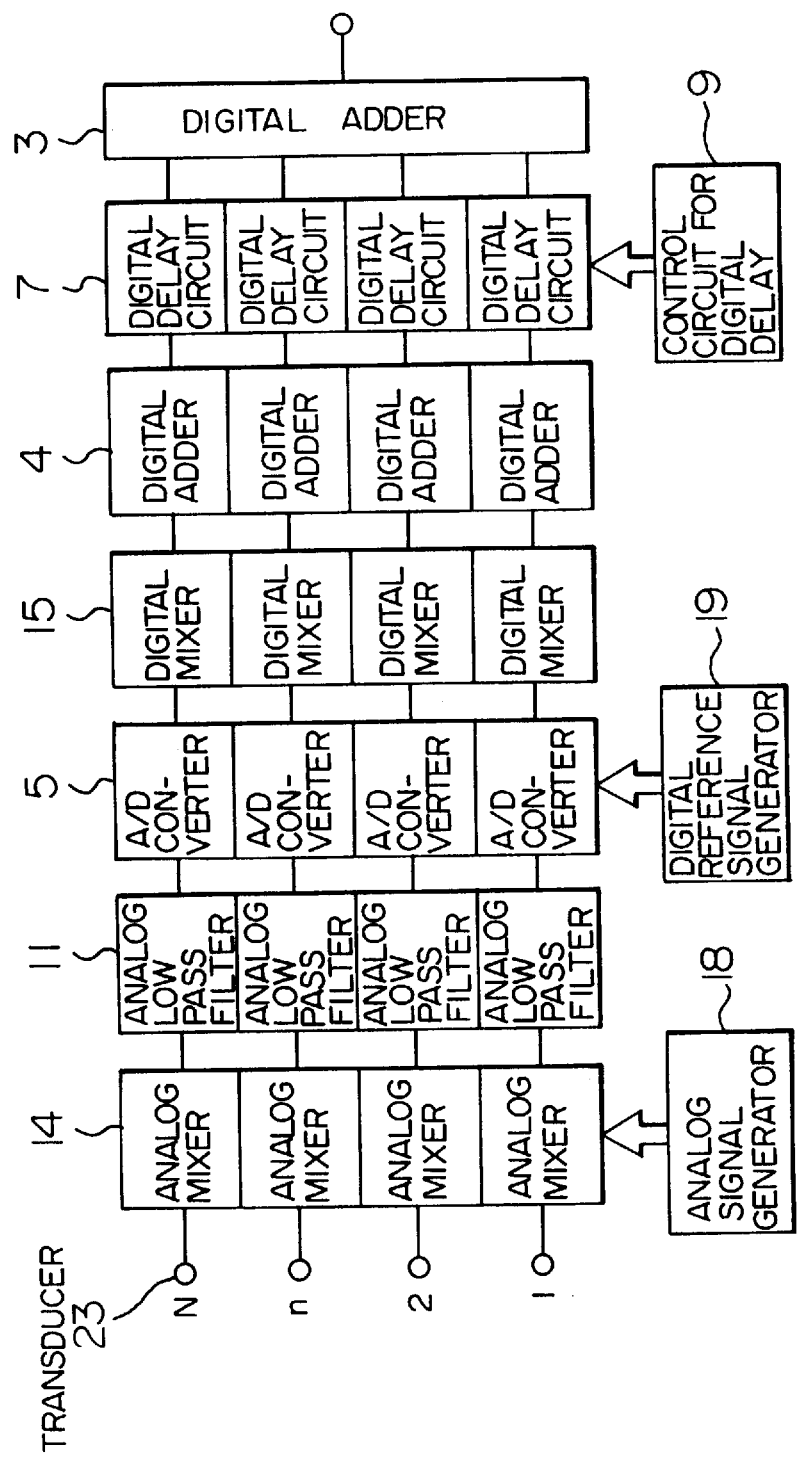
FIG. 8 is a diagram showing a configuration of an ultrasound signal processor according to a second embodiment of the present invention.

FIG. 8 is a diagram showing a configuration of an ultrasound signal processor according to a second embodiment of the present invention. In FIG. 8, reference numeral 14 designates an analog mixer, 11 denotes an analog low pass filter, 5 represents an analog to digital converter, 15 designates a digital mixer, 4 denotes a digital adder for cumulation, 7 designates a digital delay circuit and 3 denotes a digital adder. Reference numeral 18 designates an analog reference signal generator used when a receiving signal is subjected to analog mixing at the analog mixer 14, 19 designates a digital reference signal generator used when a receiving signal having undergone analog to digital conversion is subjected to digital mixing at the digital mixer 15, and 9 designates a control circuit for digital delay. A receiving signal at an n-th element is given by $$f_n(t)=A_n(t-\tau_n)[exp\{j(\omega_s t-\phi_n)\}+exp\{-j(\omega_s t-\phi_n)\}] \quad (9)$$

Real number expression of equation (9) is $$f_n(t)=2A_n(t-\tau_n)COS(\omega_s t-\phi_n) \quad (10)$$

Multiplication of the signal of equation (10) by a reference signal $m_n(t)$ generated from the analog reference signal generator 18 is carried out at the analog mixer 14. For simplicity, on the assumption that the phase of $m_n(t)$ is 0(zero) at t=0, there results $$m_n(t)=COS(\omega_a t) \quad (11)$$

and the multiplication at the analog mixer 14 becomes multiplication of real number. Accordingly, a multiplication result $O_n(t)$ is given by $$O_n(t) = f_n(t)m_n(t) \quad (12)$$
$$= A_n(t-\tau_n)[\cos\{[\omega_s + \omega_a)t - \phi_n\} + \cos\{(\omega_s - \omega_a)t - \phi_n\}]$$

and this is passed through the analog low pass filter 11 to provide $$O_n(t)=A_n(t-\tau_n)COS\{(\omega_s-\omega_a)t-\phi_n\} \quad (13),$$

which is returned to complex expression to provide $$O_n(t)A_n(t-\tau_n)[exp\{j((\omega_s-\omega_a)t-\phi_n)\}+exp\{-j((\omega_s-\omega_a)t-\phi_n)\}] \quad (14).$$

In equation (14), $\omega_s$ in equation (9) is substituted by $\omega_s-\omega_a$, indicating that the center frequency of the receiving signal is decreased from $\omega_s$ to $\omega_s-\omega_a$ and when $\omega_s$ is large, components following the analog to digital converter 5 can be constructed easily. Then, by newly taking $\omega_s-\omega_a$ for $\omega_s$, signal processings after equation (14) become identical to those explained with reference to equations (3) and (7). The reference signal from the analog reference signal generator 18 may otherwise be defined by $$m_n(t)=COS(\omega_a t-\phi_n) \quad (15).$$

In this case, the output of the analog low pass filter 11 is given by $$O_n(t)=A_n(t-\tau_n)COS\{(\omega_s-\omega_a)t\} \quad (16).$$

As described above, by newly taking $\omega_s-\omega_a$ for $\omega_s$, multiplication at the digital mixer 15 is defined as $$h_n(t)=exp(-j\omega_s t) \quad (17),$$

which is common to the respective elements.

The frequency of the reference signal participating in the multiplication in the analog mixer 14 will be described. The spectrum of s(t) is assumed to be a spectrum a as shown in FIG. 9. Like FIG. 7, spectrum aliasing at a period of the sampling frequency of the analog to digital converter is omitted. BW represents a band width of an envelope. Since in the analog mixer 14 the multiplication by $\cos(\omega_a t)$ is effected, the output spectrum of the analog low pass filter 11 becomes a spectrum b as shown in FIG. 9. If in this case two envelope spectra lying at positive and negative frequencies overlap, the envelope cannot be reconstructed in the ensuing operation. Accordingly, in order to completely reconstruct the envelope, a condition as expressed by $$\omega_a \leq \omega_s-(BW/2) \quad (18)$$

is needed. In this case, too, if beat-down of the center frequency of s(t) has precedence over slight overlapping of the envelope spectra, equation (18) need not be satisfied.

The following description will proceed on the assumption that the center frequency $\omega_s-\omega_a$ of the receiving signal shifted to a lower frequency by analog beat-down is taken for new $\omega_s$. The $h_n(t)$ is defined as $$h_n(t)=exp\{-j(\omega_s t-\phi_n)\} \quad (19)$$

in equation (3), but it may not be a complex variable function but may be a real variable function. In such a case, $h_n(t)$ is given by $$h_n(t)=COS(\omega_s t-\phi_n) \quad (20)$$

A multiplication result $g_n(t)$ is given by $$g_n(t) = f_n(t)h_n(t) \quad (21)$$
$$= A_n(t-\tau_n)[1 + \cos\{2(\omega_s t-\phi_n)\}].$$

When only the low frequency component is taken into consideration, $G_n(t)$ is given by equation (5) as in the preceding description.

A case where $\omega_s$ and $\tau_n$ are unknown and approximate value $\omega_m$ of $\omega$ and the time difference between the receiving signal of each element and a standard receiving signal are known will now be described. Thus, when the standard receiving signal is $f_l(t)$, $\tau_n-\tau_l$ is known. In this case, $h_n(t)$ is given by $$h_n(t)=exp[-j\{\omega_m t-(\omega_m+\omega_a)(\tau_n-\tau_l)\}] \qquad (22).$$

The low frequency component of multiplication result $g_n(t)$ is expressed by $$G_n(t)=A_n(t-\tau_n)exp[+j\{(\omega_s-\omega_m)(t-\tau_n)-(\omega_m+\omega_a)\tau_l\}] \qquad (23).$$

When a signal obtained by delaying equation (23) by $\tau_l-\tau_n$ is $V_n(t)$, there results $$V_n(t) \ g_n(t+\tau_n-\tau_1) = A_n(t-\tau_1)exp\ [+j\ \{(\omega_s-\omega_m)(t-\tau_1)$$

$$(\omega_m+\omega_a)\tau_1\}] \qquad (24)$$

$$= A_n(t-\tau_1)exp[+j\{(\omega_s-\omega_m)t-\phi_1\}],$$

whose amplitude is proportional to a common waveform $(A_o(t))$, where $\phi_l=-(\omega_s+\omega_a)\tau_l$. Since equation (24) is a complex number, the envelope can be obtained in terms of an absolute value of the complex number. A real variable function form of equation (22) is $$h_n(t)=COS\{\omega_m t-(\omega_m+\omega_a)(\tau_n-\tau_l)\} \qquad (25).$$

Then, $V_n(t)$ becomes $$V_n(t)=A_n(t-\tau_l)COS\{(\omega_s-\omega_m)t-\phi_l)\} \qquad (2\ 6).$$

In equation (26), the envelope cannot be determined when $\omega_s$ and $\omega_m$ are nearly equal to each other because $\phi_l$ is unknown. However, if $\omega_s$ and $\omega_m$ are made to differ suitably from each other so that, in spectra in equation (26), envelope spectra centered on frequencies $\pm(\omega_s-\omega_m)$ may not overlap, the envelope can be determined. Even in such a case, a trigonometric function indicative of a carrier signal of the receiving signal remains and hence an additional detection processing is required after the processing by the digital adder 3.

The case where $\omega_s$ and $\tau_n$ are known and approximate value $\omega_m$ of $\omega_s$ and the time difference $\tau_n-\tau_l$ between the receiving signal of each element and the standard receiving signal are known has been described, but signal processings for cases where $\omega_s$ and the time difference $\tau_n-\tau_l$ between the receiving signal of each element and the standard receiving signal are known and where approximate value $\omega_m$ of $\omega_s$ and $\tau_n$ are known can be analogized easily from the present embodiment.

Third Embodiment

Figure 10:
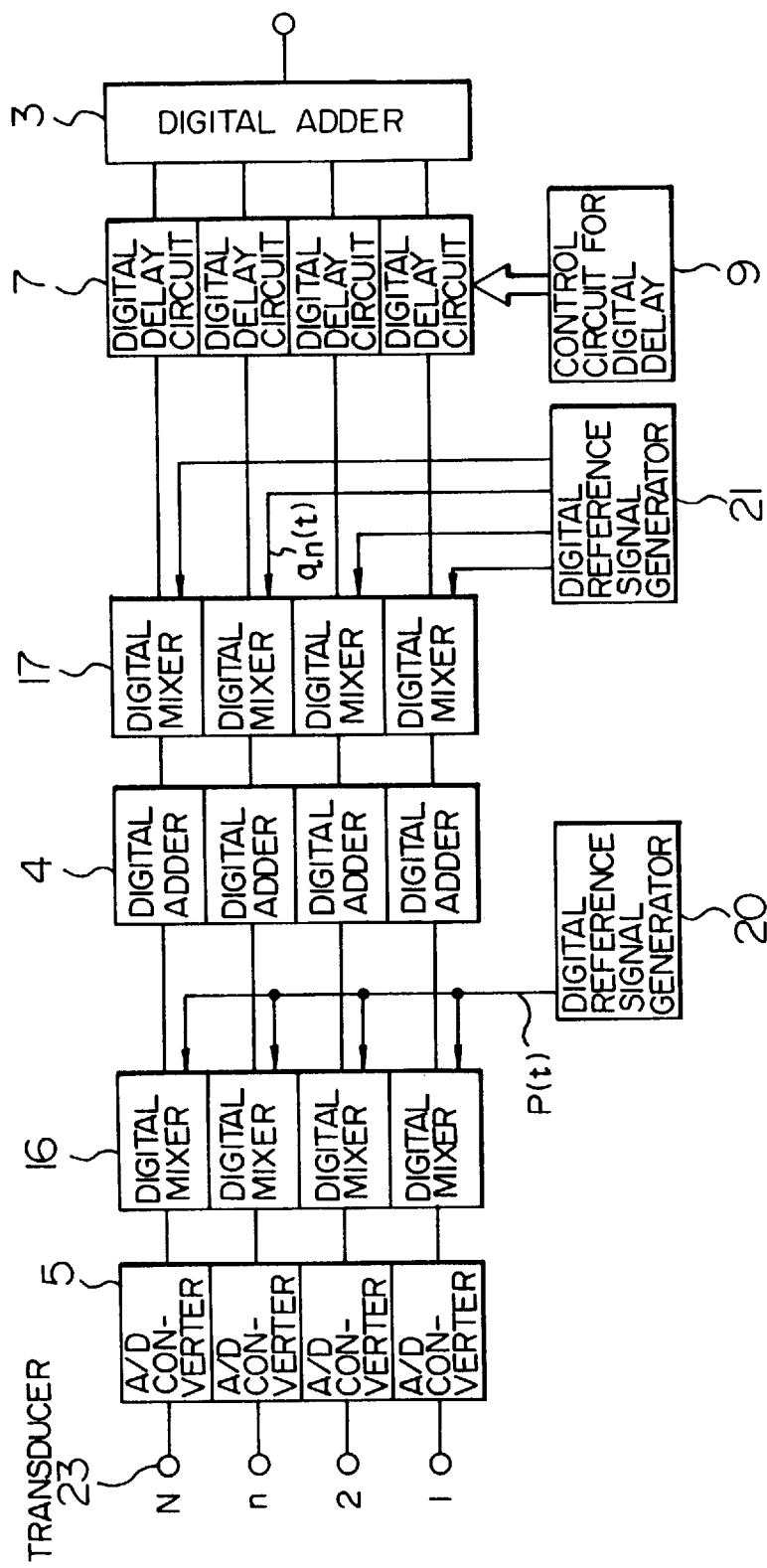
FIG. 10 is a diagram showing a configuration of an ultrasound signal processor according to a third embodiment of the present invention.

FIG. 10 is a diagram showing a configuration of an ultrasound signal processor according to a third embodiment of the present invention. The present embodiment is a further modification of the first embodiment shown in FIG. 1. Namely, the multiplication of equation (3) by $h_n(t)$ is decomposed as below $$h_n(t) = exp\{-j(\omega_s t-\phi_n)\} \qquad (27)$$
$$= exp\{-j\omega_s t\}exp(j\phi_n)$$

so as to be considered as two multiplying operations which permit a configuration as shown in FIG. 10. The decomposition of $h_n(t)$ into the two multiplying operations is allowed only when the $h_n(t)$ is a complex variable function. In FIG. 10, reference numerals 16 and 17 designate digital mixers for multiplication which substitute for that carried out by the digital mixer 15 in FIG. 1. Denoted by 20 and 21 are digital reference signal generators used during digital mixing at the digital mixers 16 and 17. A signal waveform p(t) used for initial digital mixing by the digital mixer 16 is common to the respective elements and is $$p(t)=exp(-j\omega_s t) \qquad (28).$$

In the digital mixer 17, multiplication by a digital reference signal (which is different for each element)

$$q_n(t)=exp(j\phi_n) \qquad (29)$$

generated from the digital reference signal generator 21 is effected to compensate mutual phase difference. In this configuration, by providing arrangements each composed of only the digital mixer 17 and ensuing components in parallel or performing a multiplexing processing, signals from a plurality of positions in an object to be tested can be received simultaneously.

Figure 11:
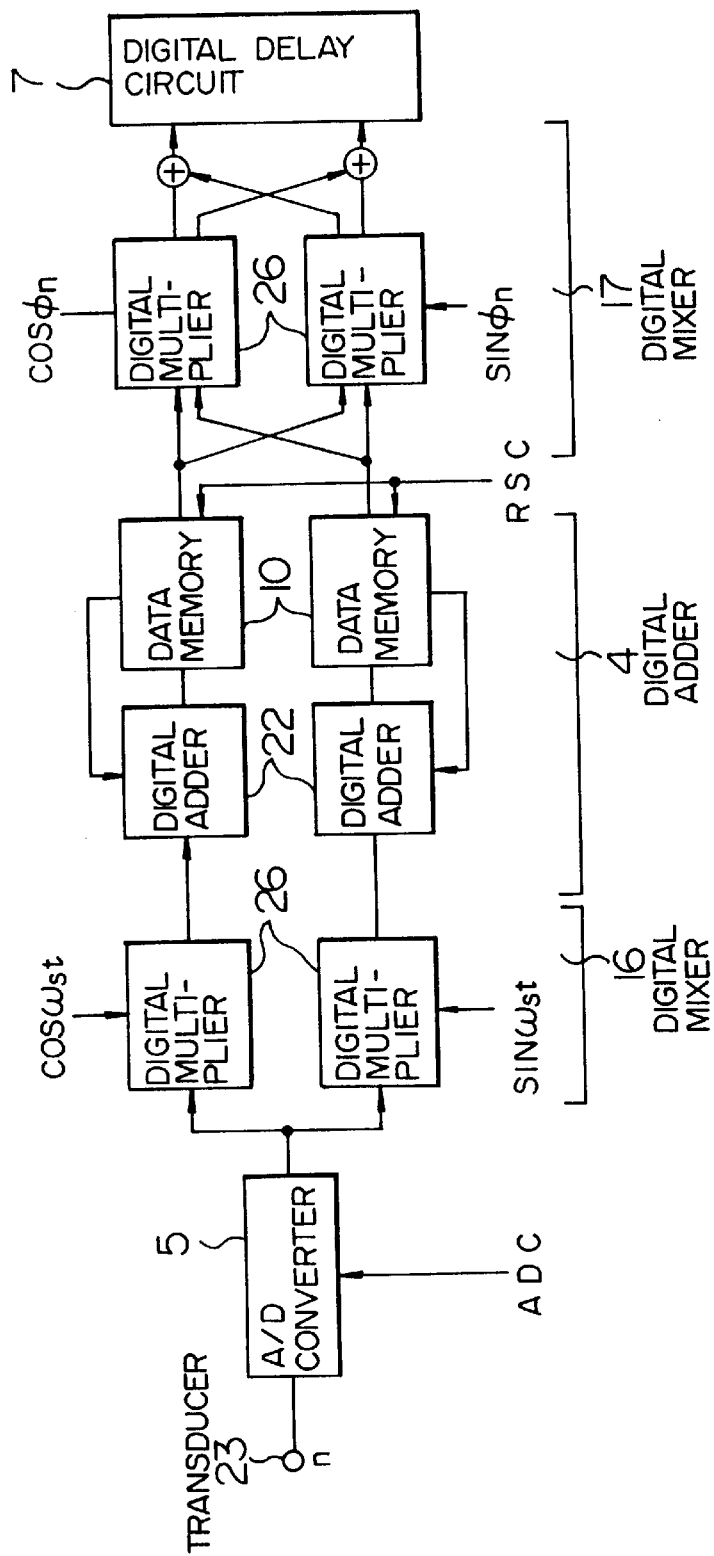
FIG. 11 is a diagram showing a configuration for processing of a single channel signal in the third embodiment of the present invention.
Figure 12:
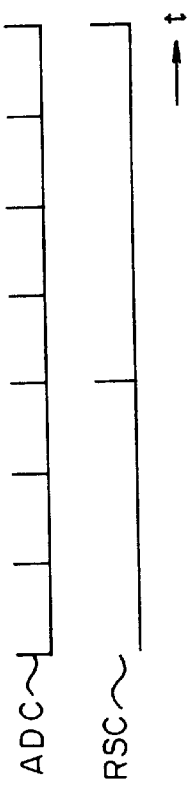
FIG. 12 is a diagram showing timing of a control signal in the third embodiment of the present invention.

FIG. 11 is a diagram showing a configuration for processing of a single channel signal in the third embodiment of the present invention. In FIG. 11, digital multipliers 26 corresponding to the digital mixers 16 and 17 in FIG. 10 use reference signals, 90° out of phase from each other, to perform multiplication. Digital mixer 17 multiplies complex output of digital adder 4 by complex digital reference signal $exp(j\phi_n)$, and digital mixer 17 is composed of four elemental digital multipliers and two digital adders, for its figure being simplified. 22 denotes digital adders for cumulation and 10 designates memories for temporary storage of results of addition at the digital adders 22 and which correspond to the digital adder 4 for cumulation addition in FIG. 10. The time relation between control signals is illustrated in FIG. 12. In the present embodiment, an analog to digital conversion (A/D conversion) command ADC and a command for ending cumulation and delivering results (cumulation/output) RSC are made to be synchronous with the transmitting signal to suppress noises. In FIG. 10, by changing, with time, control data generated by the digital reference signal generator 21 and the control circuit 9 for digital delay, the focal position can be shifted continuously.

Figure 13:
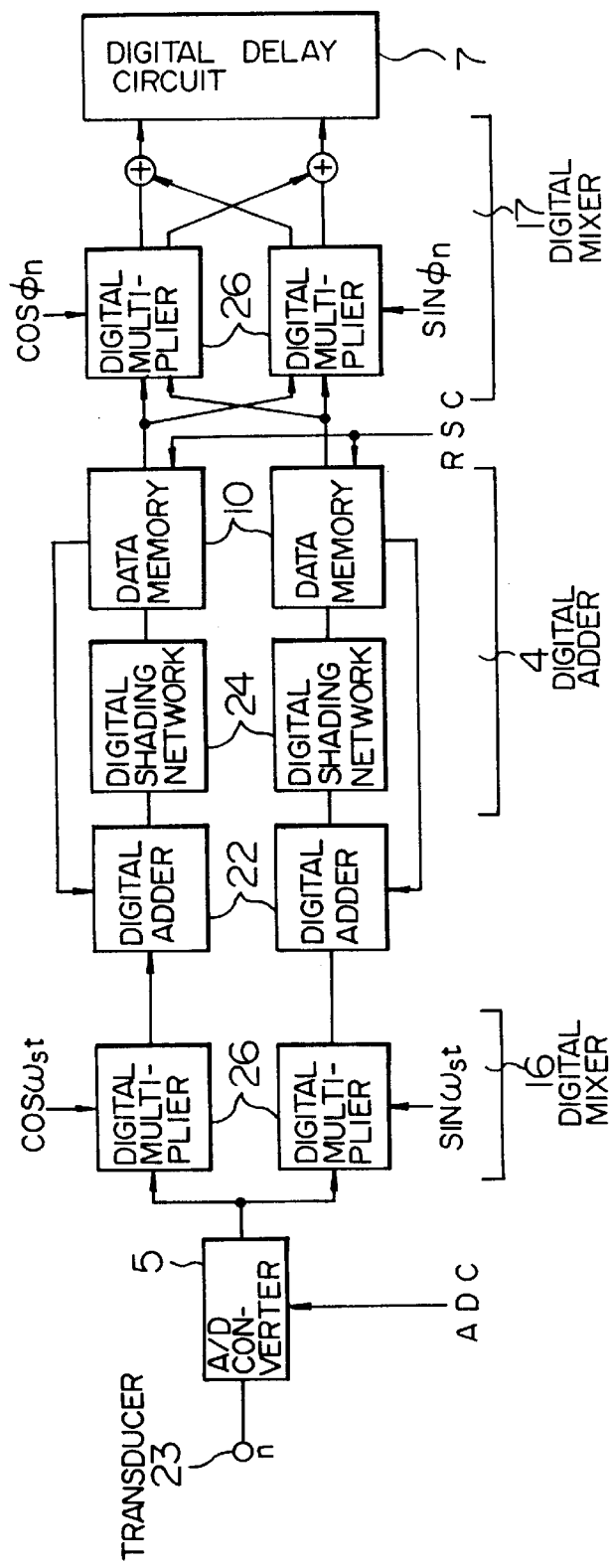
FIG. 13 is a diagram showing another configuration for processing of a single channel signal in the third embodiment of the present invention.
Figure 14:
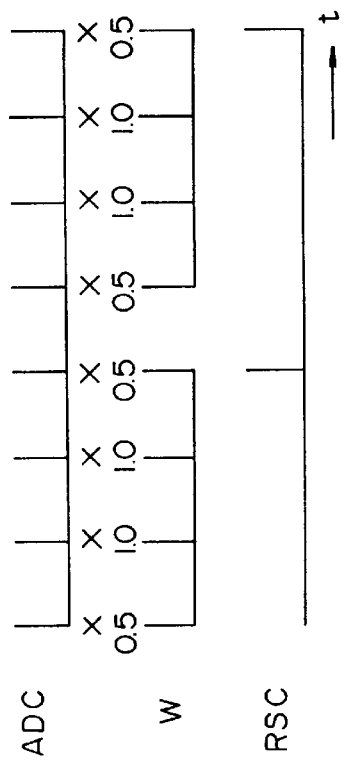
FIG. 14 is a diagram showing timing of a control signal in the third embodiment of the present invention.

FIG. 13 is a diagram showing another configuration for processing a single channel signal in the third embodiment of the present invention. In the present embodiment, digital shading networks 24 are interposed between the digital adders 22 for cumulation and the temporary memories 10 so that individual data pieces may be shaded differently during addition. Through this, the time relation among control signals (an analog to digital conversion (A/D conversion) command ADC, a command for ending cumulation and delivering results (cumulation/output) RSC and a digital shading generation command W) is set up as shown in FIG. 14 to ensure that digital data pieces individually shaded by the digital shading network 24 are added and delivered.

Fourth Embodiment

FIG. 15 is a diagram showing a configuration of an ultrasound signal processor according to a fourth embodiment of the present invention. The present embodiment is a further modification of the second embodiment shown in FIG. 8 and essentially, in the present embodiment, the configuration of the third embodiment shown in FIG. 10 is added with the analog mixer 14, analog reference signal generator 18 and analog low pass filter 11 shown in FIG. 8.

Figure 16:
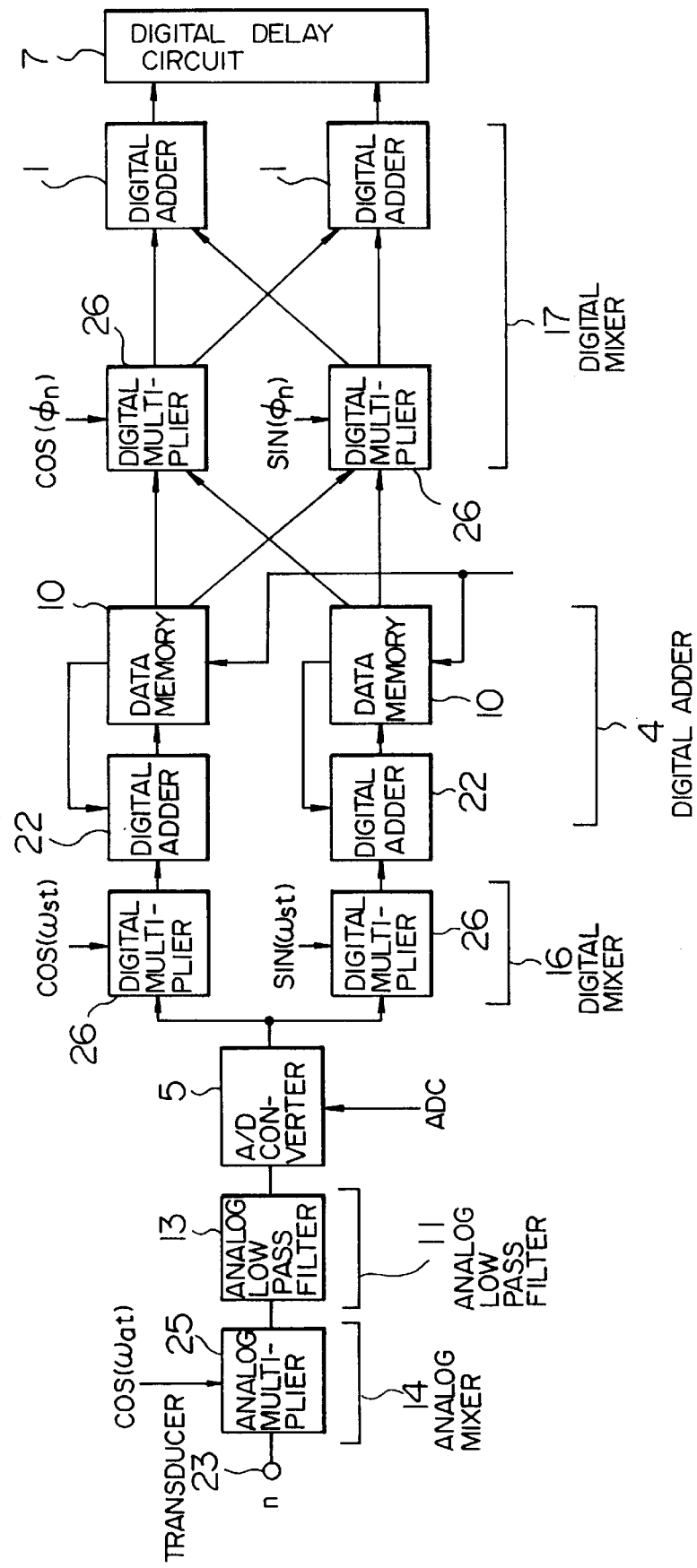
FIG. 16 is a diagram showing a configuration for processing of a single channel signal in the fourth embodiment of the present invention.

FIG. 16 is a diagram showing a configuration for processing of a single channel signal in the fourth embodiment of the present invention. In FIG. 16, an analog multiplier 25 corresponds to the analog mixer 14 in FIG. 15, an analog low pass filter 13 corresponds to the analog low pass filter 11 in FIG. 15, and digital multipliers 26 correspond to the digital mixers 16 and 17 in FIG. 15 and perform multiplication by using reference signals which are 90° out of phase from each other. 1 denotes digital adders for complex multiplication. 22 designates digital adders for cumulation and 10 denotes memories for temporary storage of addition results of the digital adders 22, the adders 22 and memories 10 corresponding to the digital adder 4 for cumulation addition of FIG. 15. Like the third embodiment, the time relation between control signals (ADS and RSC) is set up as shown in FIG. 12 and the ADC and RSC are made to be synchronous with the transmitting signal to suppress noises. Also, as in the case of the third embodiment, by changing, with time, control data pieces generated by the digital reference signal generator 21 and the control circuit 9 for digital delay, the focal position can be shifted continuously.

Figure 17:
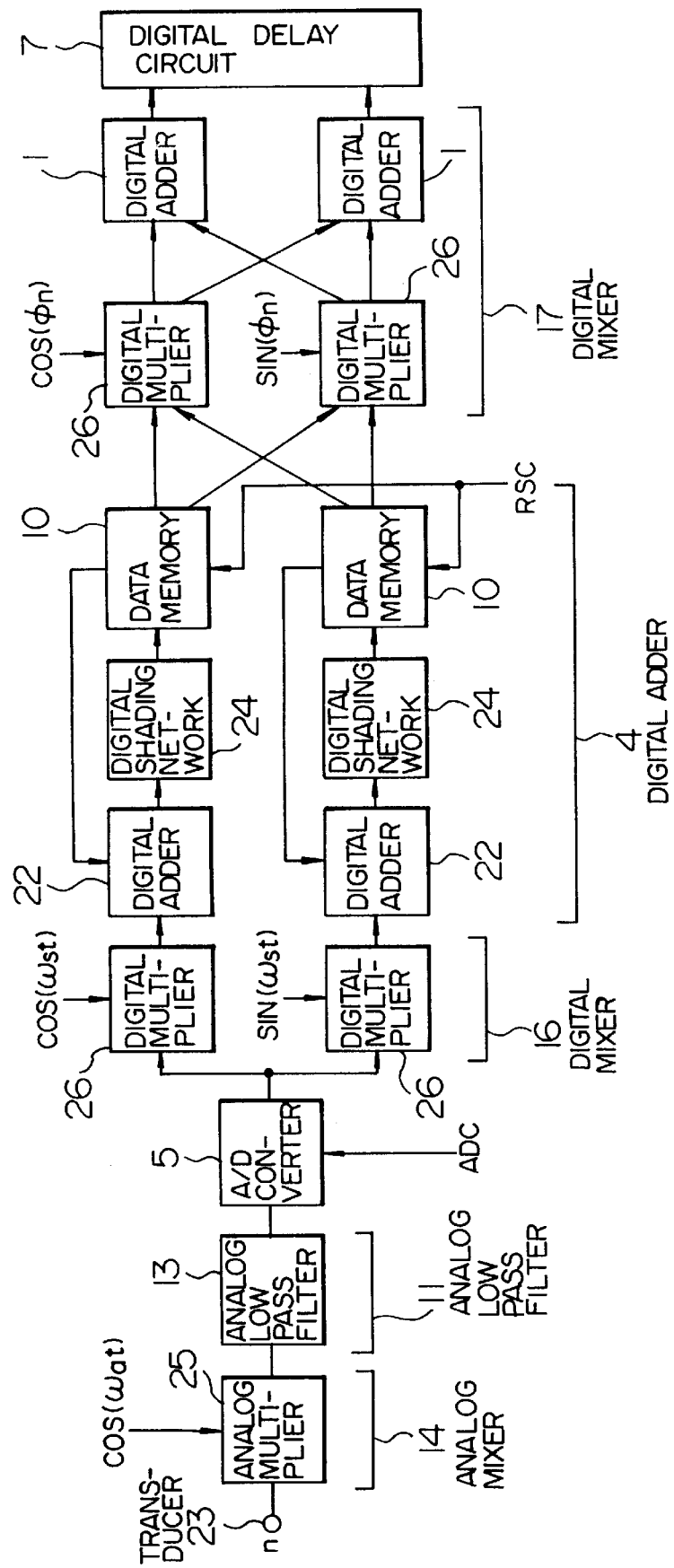
FIG. 17 is a diagram showing another configuration for processing of a single channel signal in the fourth embodiment of the present invention.

FIG. 17 is a diagram showing another configuration for processing of a single channel signal in the fourth embodiment of the present invention. In the present embodiment, like the configuration shown in FIG. 13, digital shading networks 24 are interposed between the digital adders 22 for cumulation and the temporary memories 10 so that individual data pieces may be shaded differently during addition. As in the case of FIG. 13, the time relation among control signals is set up as shown in FIG. 14 to ensure that digital data pieces individually shaded by the digital shading networks 24 are added and delivered.

Fifth Embodiment

Arrangements adapted to perform a processing of the digital mixer 17 and the ensuing processings shown in FIG. 13 are provided in parallel as will be described below.

Figure 18:
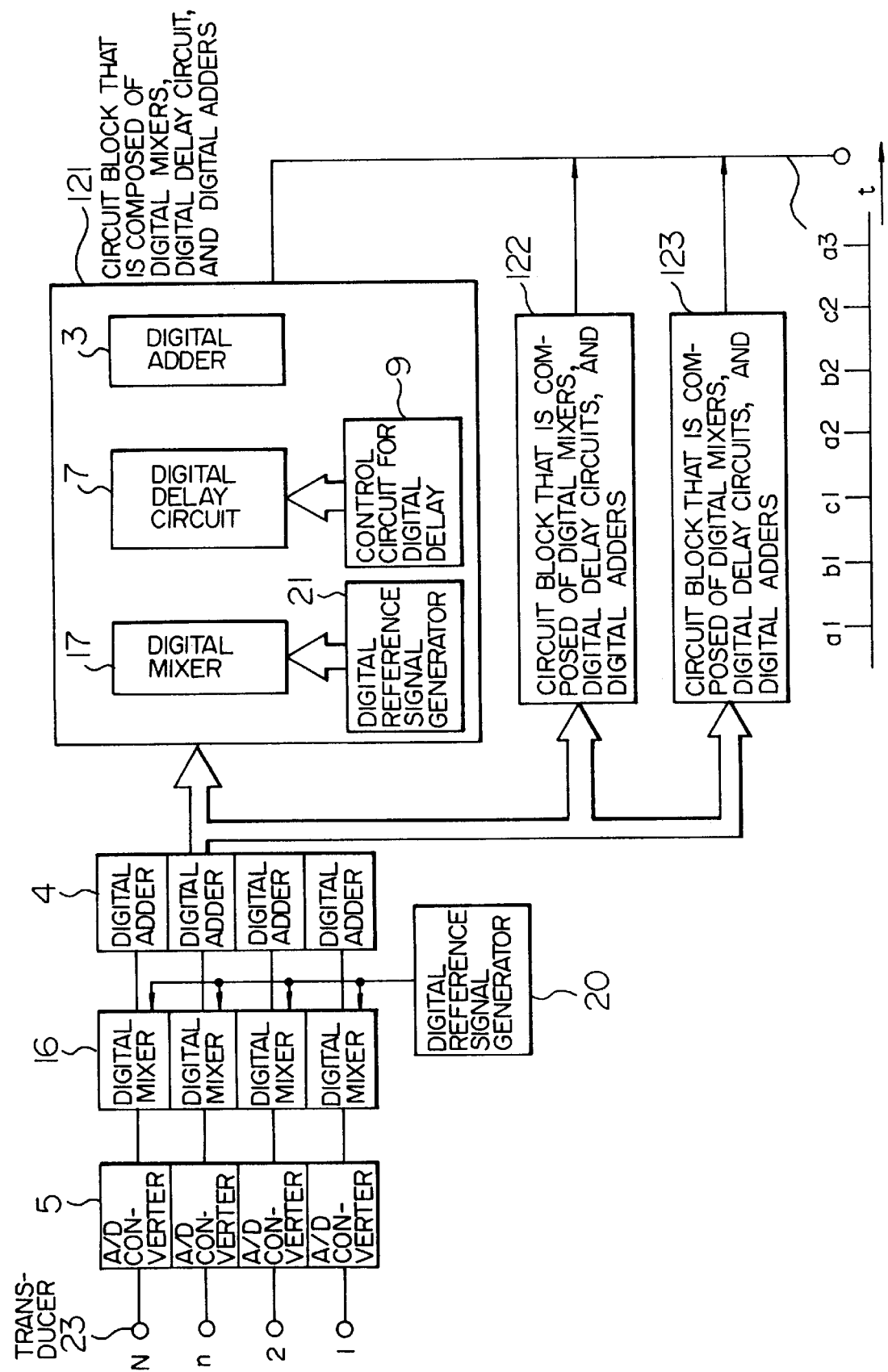
FIG. 18 is a diagram showing a configuration of an ultrasound signal processor according to a fifth embodiment of the present invention.

FIG. 18 is a diagram showing a configuration of an ultrasound signal processor according to a fifth embodiment of the present invention. In FIG. 18, reference numerals used in FIG. 10 designate like components and blocks 121 to 123 having each digital mixers 17, digital delay circuits 7 and digital adders 3 are connected in parallel. Denoted by $a_1$ to $a_3$ are outputs from the block 121, by $b_1$ and $b_2$ are outputs from the block 122 and by $c_1$ and $c_2$ are outputs from the block 123, the outputs indicating signal values corresponding to an ultrasound beam formed by each block. By providing the three delay/addition arrangements in parallel after the digital mixers 4 for cumulation, receiving beams in three different directions can be formed on time division basis.

Sixth Embodiment

Figure 19:
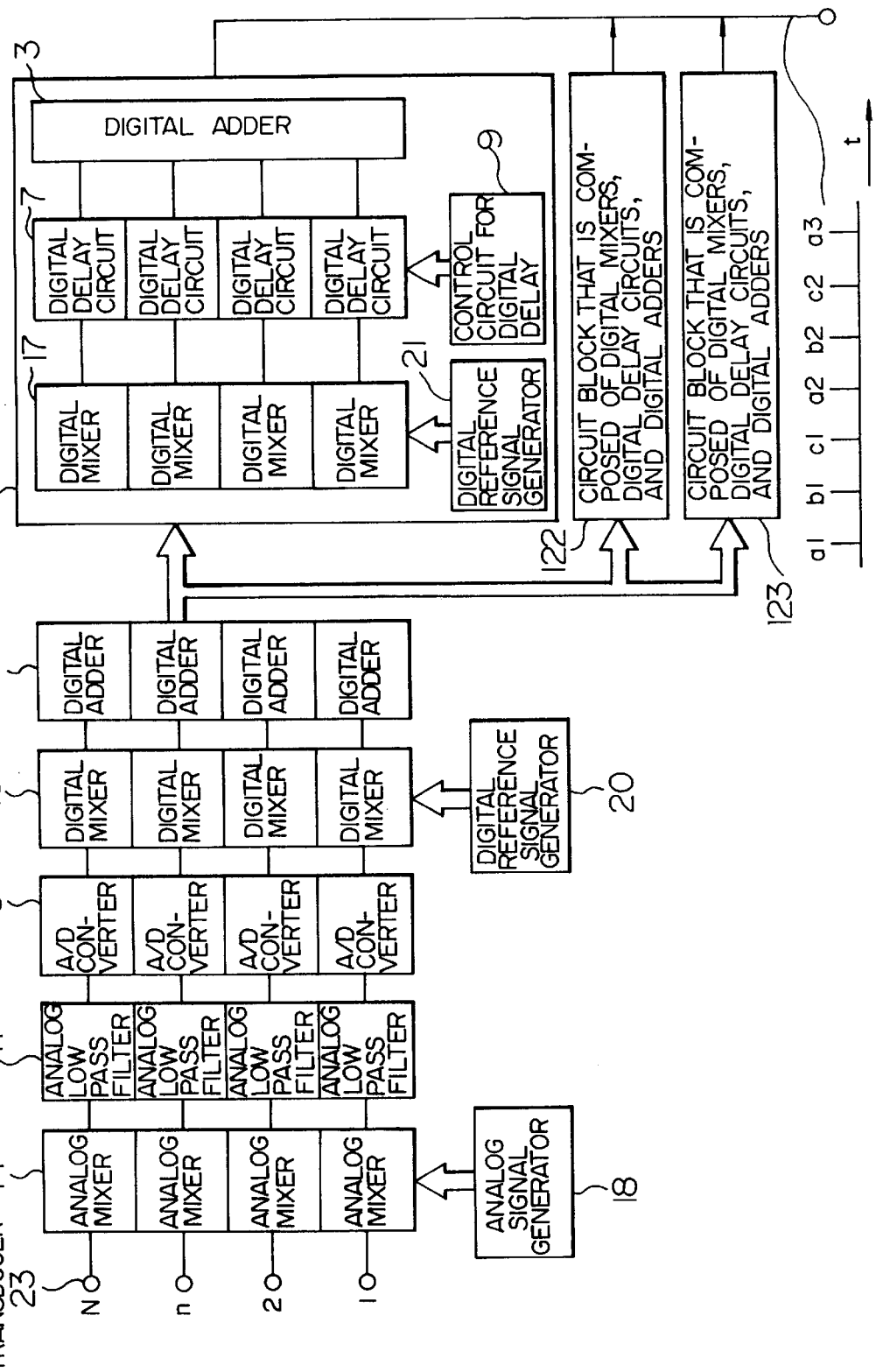
FIG. 19 is a diagram showing a configuration of an ultrasound signal processor according to a sixth embodiment of the present invention.

FIG. 19 is a diagram showing a configuration of an ultrasound signal processor according to a sixth embodiment of the present invention. Essentially, in the present embodiment, the analog mixer 14, analog reference signal generator 18 and analog low pass filter 11 shown in FIG. 8 are added to the configuration of the fifth embodiment shown in FIG. 18.

Seventh Embodiment

A configuration for storing all signals after the over-sampling processing to effect focus adjustment will now be described.

Figure 20:
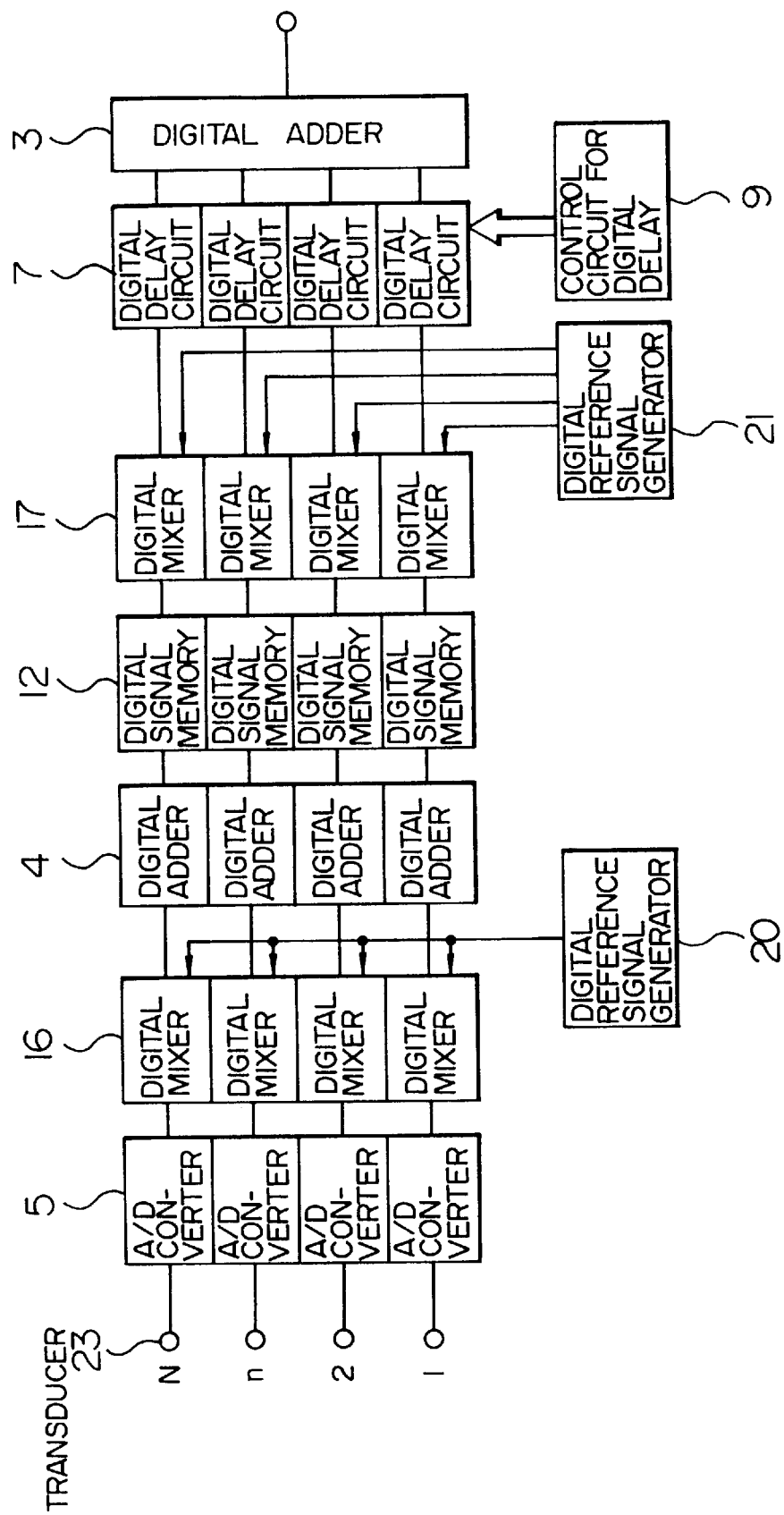
FIG. 20 is a diagram showing a configuration of an ultrasound signal processor according to a seventh embodiment of the present invention.

FIG. 20 is a diagram showing a configuration of an ultrasound signal processor according to a seventh embodiment of the present invention. In FIG. 20, digital signal memories 12 are interposed between digital adders 4 for cumulation and digital mixers 17. The memory is adapted to efficiently store data necessary for performing focus adjustment based on adaptive image reconstruction. A signal after the over-sampling processing preserves all information pieces within a band of a receiving signal which are caused by beat-down to be preserved within a low frequency band, and therefore fore the number of storing data pieces representative of the signal is compressed. By performing phase correction of the signal from the digital mixer 17 and time shift by the digital delay circuit 7 carried out in a complimentary manner to the phase correction, a beam forming method complying with conditions of an object to be imaged can be realized. Through this, delay time $\tau_n$ applied to one receiving element after another can be changed in expectation of the fact that, for example, the speed of sound sightly changes from one portion to another within an object to be tested.

Eighth Embodiment

Figure 21:
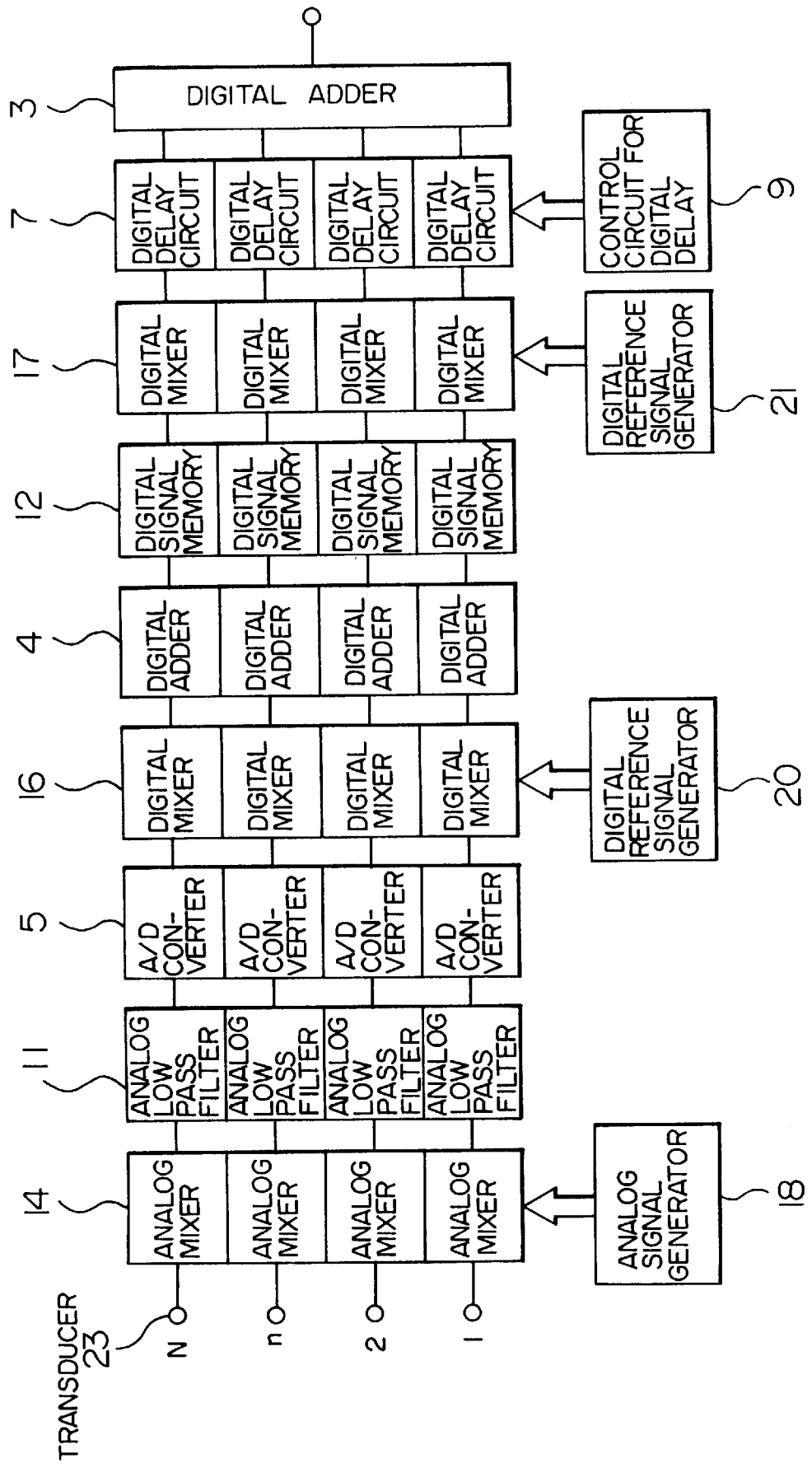
FIG. 21 is a diagram showing a configuration of an ultrasound signal processor according to an eighth embodiment of the present invention.

FIG. 21 is a diagram showing a configuration of an ultrasound signal processor according to an eighth embodiment of the present invention. Essentially, in the present embodiment, the analog mixer 14, analog reference signal generator 18 and analog low pass filter 11 are added to the configuration of the seventh embodiment shown in FIG. 20.

In the second, fourth, sixth and eighth embodiments described previously, the configuration of the analog to digital converter for handling an ultrasound signal having a higher center frequency than that in the first, third, fifth and seventh embodiments can be simplified.

In the respective embodiments described as above, the frequency of a receiving signal after the analog beat-down is made to be coincident with that of a digital reference signal but the present invention is in no way limited thereto and the frequency of the digital reference signal may be changed with time.

Figure 22:
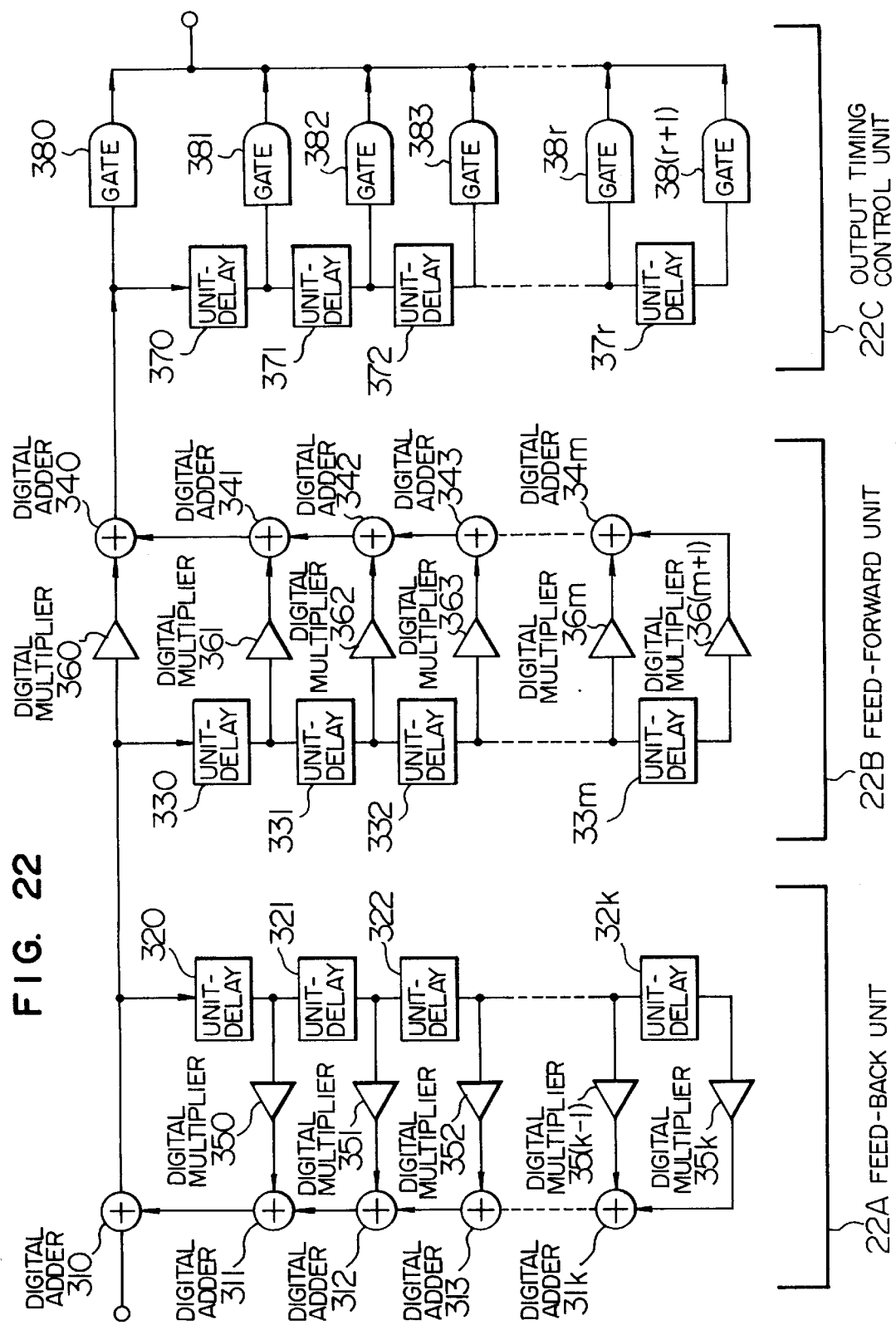
FIG. 22 is a diagram showing another configuration for realizing cumulation and addition in the respective embodiments of the present invention.

The configuration of the adder 4 for cumulation is not limited to that described previously and various configurations thereof may be conceivable provided that they have the integrating effect due to addition. For example, an arrangement as shown in FIG. 22 may be employed wherein shading necessary for individual data pieces can be realized at a high degree of freedom. In FIG. 22, reference numerals 310 to 31$k$ and 340 to 34$m$ designate adders, 320 to 32$k$, 330 to 33$m$ and 370 to 37$r$ designate unit-delay circuits, 350 to 35$k$ and 360 to 36 (m +1) designate multipliers and 380 to 38(r+1) designate gates. Coefficients of the respective multipliers may be fixed or may be read out of a memory, not shown, in compliance with purposes. Denoted by k, m and r are integers, not negative, which are determined by intended configuration and scale. With this configuration, by utilizing a feed-back unit 22A or a feed-forward unit 22B, an integrating circuit having a desired frequency characteristic can be set up. Further, the output frequency and timing offset can be controlled desirably by means of an output timing control unit 22C. The scale or the presence or absence of 22A, 22B and 22C is selected as necessary. Obviously, in addition to the illustrated configuration, many configurations having the same function as that of FIG. 22 may be available.

In the respective embodiments set forth so far, the arrangement of the digital delay circuit 7 and digital mixer 17 may be changed as necessary. In the foregoing embodiments, the absolute amplitude of the reference signal envelope in the analog mixer 14 and digital mixers 15, 16 and 17 is set to 1 (one) but this is not limitative and the amplitude of the reference signal envelope may be changed for each element to shade receiving signals. In the signal processor of the present invention, the cumulation processing after the beat-down of a receiving signal is realized and the over-sampling processing acts effectively to simplify the configuration of the analog to digital converter, and the present processor can therefore be applied to various apparatus in addition to the ultrasound apparatus. In the foregoing embodiments, each of the digital circuits such as the digital reference signal generator, digital delay circuit, control circuit for digital delay, digital adder and digital mixer may be constructed by using a corresponding analog circuit, an A/D converter and/or D/A converter in combination.

Next, specific examples of construction of an apparatus for forming a multibeam (ninth to fourteenth embodiments) will be described. In a received signal processing circuit of the ultrasound signal processor of the present invention, the Nyquist sampling frequency for a received signal lowered to a baseband has a low frequency and therefore, time intervals at which data pieces for one received beam are generated are prolonged and the sampling frequency for generation of these data pieces can be decreased. When the sampling frequency is set to 1/m of a sampling frequency actually supplied to the ADC, m beam data pieces can be processed in a time sharing fashion by changing the order of data pieces processed on the time axis in one received signal processing circuit. Accordingly, a multi-direction delay unit can effect a signal processing for forming a plurality of received beams through a time sharing process in one received signal processing circuit, thereby ensuring that a received multibeam can be formed without increasing the circuit scale of the received beam forming unit.

The embodiments of the present invention will now be described in greater detail with reference to the accompanying drawings.

Ninth Embodiment

Figure 23:
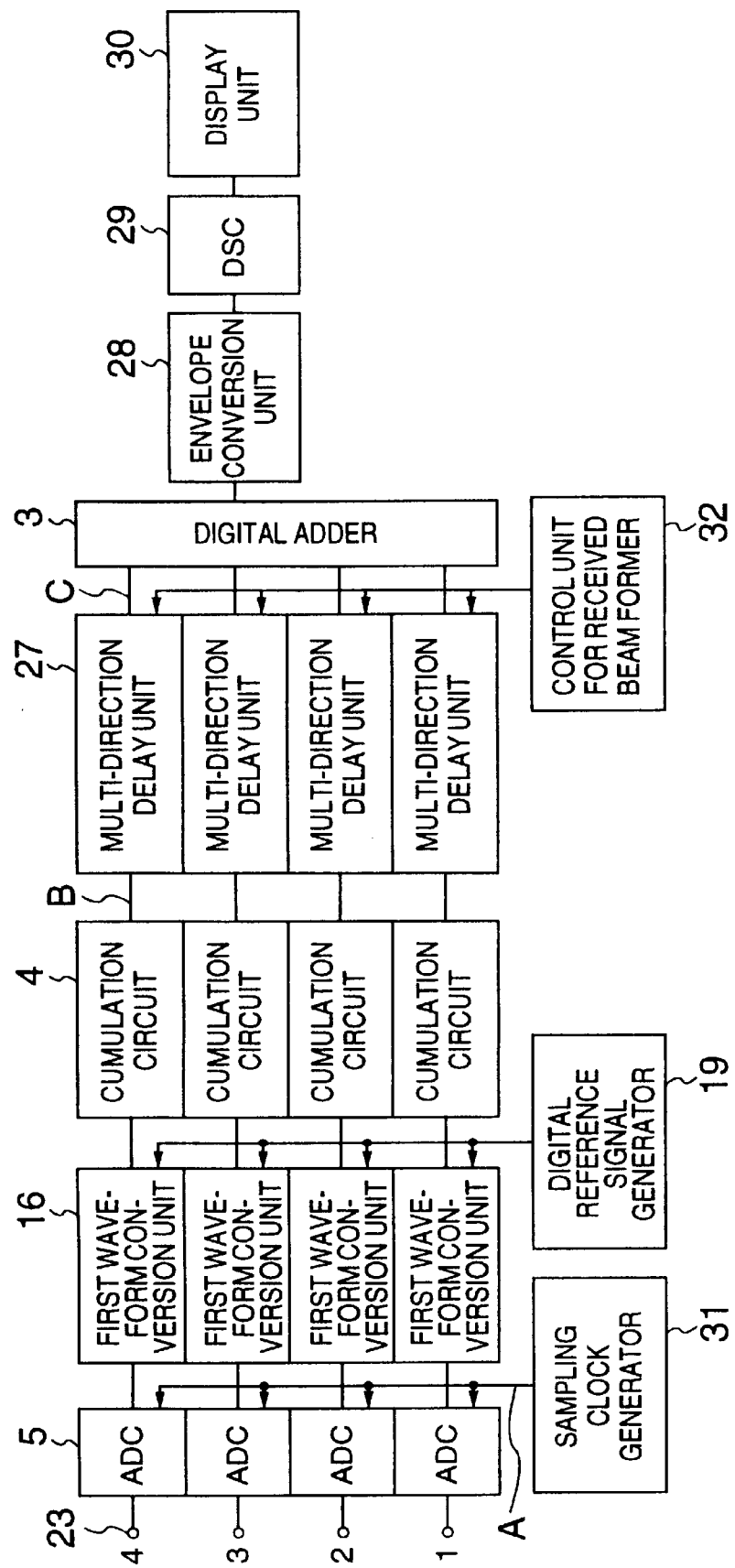
FIG. 23 is a diagram showing a construction of an essential part of an ultrasound signal processor according to a ninth embodiment of the present invention.

A construction of an essential part of an ultrasound signal processor according to a ninth embodiment of the present invention is illustrated in block form in FIG. 23. Received signals received at an array of transducers 23 are each processed by an amplifier or a variable amplifier, an analog filter or an analog filter of variable frequency band width and the like and are fed to a received signal processing unit. Here, the received signal processing unit includes analog to digital converters (ADC's) 5, first waveform conversion units (digital mixers) 16, cumulation circuits 4, and multi-direction delay units 27. For simplification of explanation, 4 channels are exemplified in FIGS. 23, 24, 29, 30, 31 and 32.

Each of the received signals fed to the received signal processing unit constructed as shown in FIG. 23 undergoes digital conversion by means of the ADC 5 constituting the received signal processing unit. A sampling clock Sck set in the ADC is generated from a sampling clock generator 31 and supplied in common to sampling clock input terminals of the ADC's of individual channels. Obviously, with packaging in mind, the sampling clock generator may be provided on each printed circuit board (on which, for example, received signal processing circuits for 20 channels each in the form of an LSI are carried). In this case, however, the sampling clocks for all channels have to be synchronous with each other.

Obviously, when the received signal processing circuits take the form of LSI's, a sampling clock may be generated from an LSI of each channel. In the received signal processing unit, a number of received signal processing circuits are arranged in parallel in order that respective received signals from the respective transducers can be processed and under this situation, the word"channel" means a received signal processing circuit supplied with one received signal.

It is known in the art that a received signal can be reconstructed when the sampling frequency for the ADC is twice or more an upper limit frequency of a frequency band width for the received signal. In the present invention, signals from the individual transducers can be sampled at a sufficiently higher frequency. A sampled received signal is then fed to the first waveform conversion unit 16 at which the sampled received signal is multiplied by a digital reference signal (center frequency $\omega_s$) generated from a digital reference signal generator 19 and a waveform of the received signal is converted into a complex signal having a difference frequency part and a sum frequency part.

The digital reference signal from the digital reference signal generator 19 is also fed in common to the respective channels. A concrete example of the first waveform conversion unit 16 (digital mixer) is shown in FIG. 26.

Figure 26:
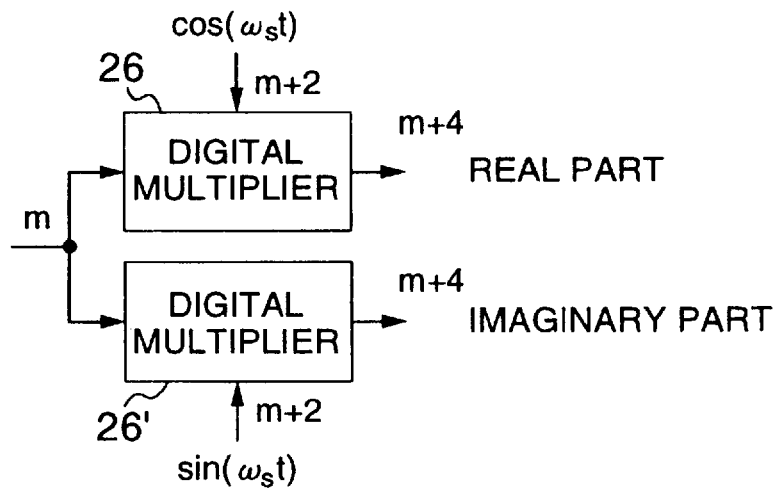
FIG. 26 is a diagram showing an example of the construction of a first waveform conversion unit.
Figure 27:
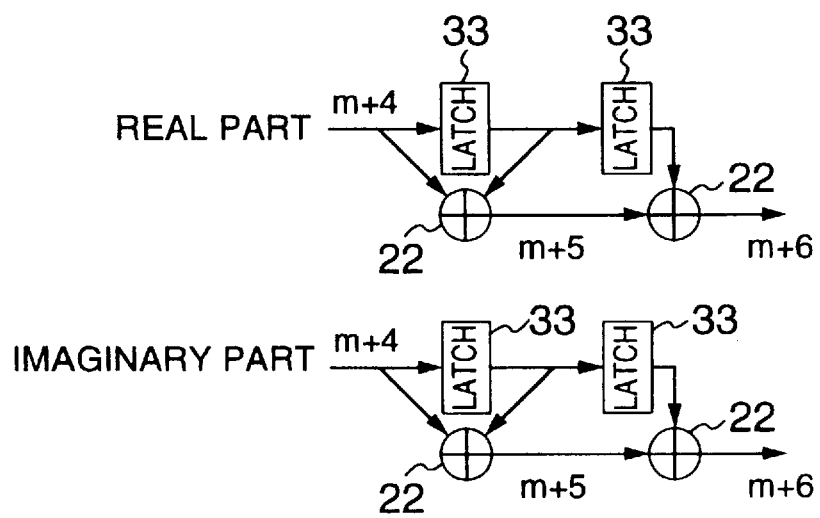
FIG. 27 is a diagram showing an example of the construction of a cumulation circuit.

In the example shown in FIG. 26, a received signal converted into m bits by means of the ADC 5 branches to two of which one is multiplied by $\cos(\omega_s t)$ by means of a digital multiplier 26 and the other is multiplied by $\sin(\omega_s t)$ by means of a digital multiplier 26'. Here, $\omega_s$ is a center frequency of the received signal. Through the signal processing shown in FIG. 26, the received signal is converted into a complex signal having a difference frequency part (difference frequency $\omega_s - \omega_s = 0$) which is a signal component of a baseband and a sum frequency part (sum frequency $\omega_s + \omega_s = 2\omega_s$). Output signals (imaginary part and real part signals) shown in FIG. 26 are fed to a cumulation circuit 4. Since the signal component of a baseband is lowered to a frequency which is sufficiently lower than the center frequency of the first received signal, even a sampling frequency identical to the sampling frequency for the ADC can ensure sampling which sufficiently satisfies the Nyquist sampling frequency for the baseband (over-sampling) and addition (cumulation) of received signals sampled in a time series fashion can be permitted. A specified example of the cumulation circuit is shown in FIG. 27.

A received complex signal of (m+4) bits is sequentially held by latches 33 and three sequential consecutive data pieces of the output signal of the circuit shown in FIG. 26 are added together in an adder 22. With the ADC supplied with the maximum amplitude, the number of bits is of course increased and (m+6) bits result. Through the addition of the received signals, quantization noise and white noise of input noise are canceled out and the signal can be nearly tripled while the noise being √3 times increased, so that the S/N can be increased by 3dB. The number of addition operations COUNT in the cumulation circuit is determined by sampling frequency $f_s$ (=ADFQ) and frequency band width BW as follows:

$$COUNT \leq (ADFQ/BW) \tag{8}$$

The envelope of the received signal can be reconstructed if a condition pursuant to equation (8) is satisfied.

In the structure shown in FIG. 27, three consecutively received signals are sequentially added and delivered and therefore the cumulation circuit is constructed so as to have a rectangular shading filter characteristic. In order to decrease an unwanted frequency component of the sum frequency part, various methods have been contrived including a method in which two stages of the structure shown in FIG. 27 are provided and triangular weight is applied in the addition (cumulation) of received signals or the number of addition operations in the preceding and succeeding stages is adjusted to apply rectangular weight. In any method, through the use of only the digital adders, various types of weight can be realized. Given that output data pieces of the first waveform conversion unit (digital multiplier) 16 in FIG. 23 are represented by Di (i is a number of the sampling clock signals), (D1+D2+D3+D2+D3+D4+D3+D4+D5)=(D1+2D2+3D3+2D4+D5) is obtained. Coefficients of Di are 1, 2, 3, 2 and 1 to represent triangular weight.

The cumulation circuit constructed as shown in FIG. 27 can provide a baseband signal of the received signal. Various delay processings are carried out using the baseband signal. Here, a signal processing is carried out in which a time difference required for ultrasound to propagate through a distance difference between a target focus position and each of the transducers is compensated in terms of time or phase by means of a multi-direction delay unit 27 to match wave fronts of echoes, received signals generated from the respective transducers are added together by means of a digital adder 3, an envelope of the received signal is determined by an envelope conversion unit 28 to provide a signal for formation of a received beam, and the direction of the received beam is changed to form received beams. The above signal processing is repeated to scan the received beam to provide a display on a display unit 30 by means of a digital scan converter (DSC) 29.

Figure 24:
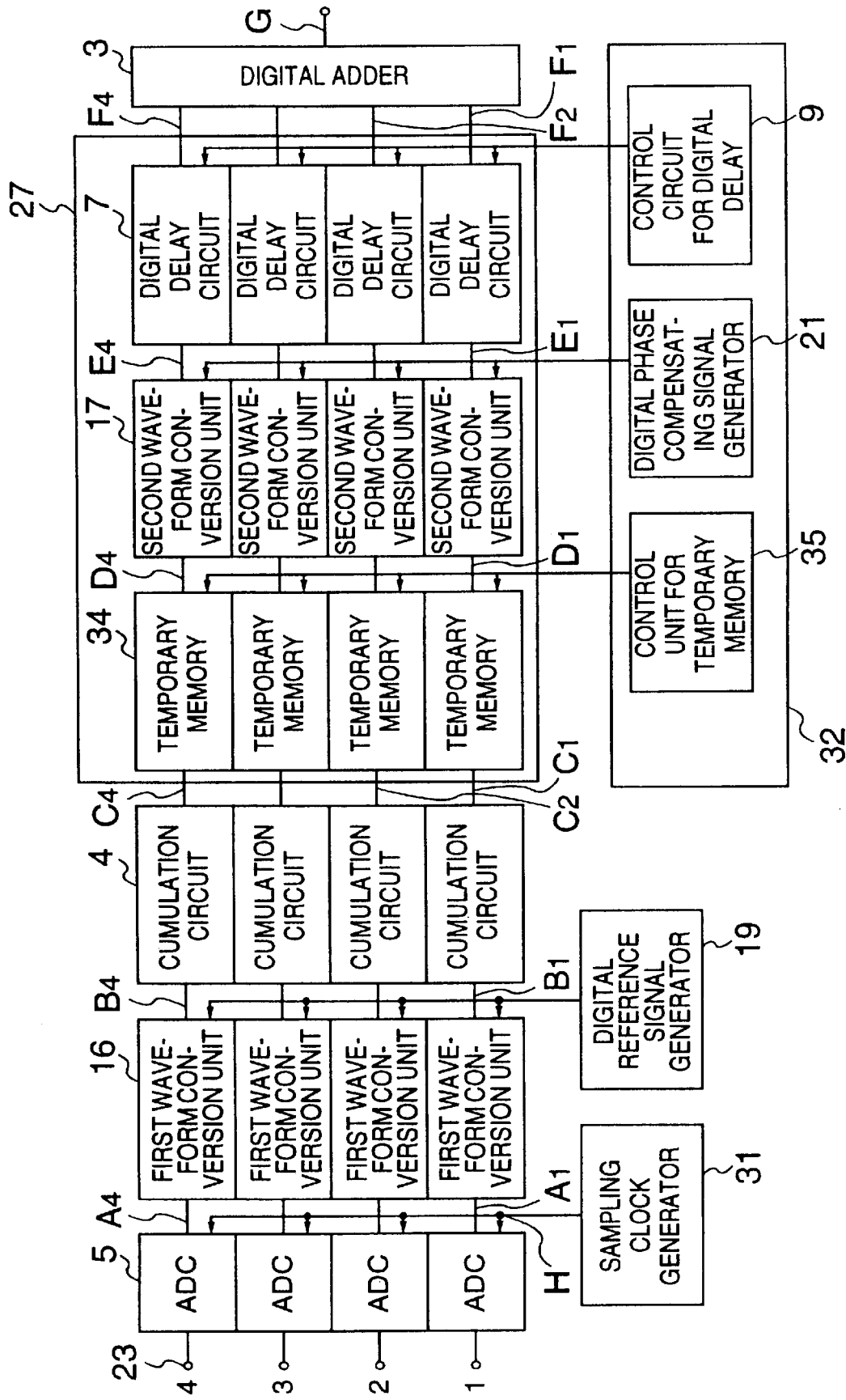
FIG. 24 is a diagram showing a construction of an essential part of an ultrasound signal processor according to a tenth embodiment of the present invention.

The multi-direction delay unit 27 is constructed as exemplified in FIG. 24. In this example, each received signal processed by the cumulation circuit 4 is temporarily stored in a temporary memory 34 in order that received signals of the same Ri are saved, under the control of a control unit for temporary memory 35, so as to be used for formation of a plurality of received beams, and the received signals Ri necessary for-formation of the received beams are delivered out of the temporary memory to form a received multibeam in a time sharing fashion.

Tenth Embodiment

Figure 25:
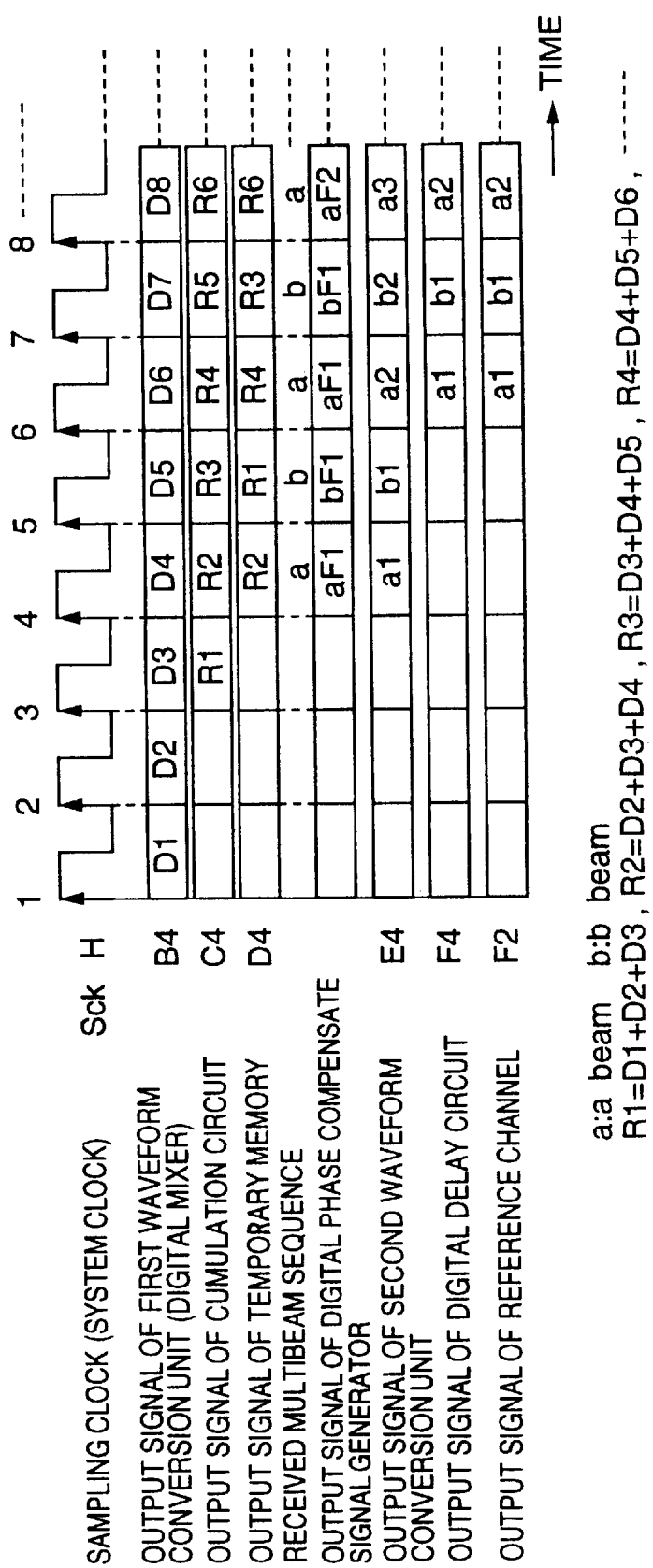
FIG. 25 is a time sequence chart in the tenth embodiment.

A sequence of multibeam formation according to a tenth embodiment of the present invention will now be described. Illustrated in FIG. 25 is an example of a sequence in which after one transmission operation of ultrasonic wave, a plurality of ultrasound received beams are formed from a received signal received at each of the transducers forming a receiving aperture, thereby forming received beams in two different directions. In FIG. 25, timings of output signals from the respective signal processing units are illustrated by taking a fourth channel, for instance, but the same holds true for another channel. A signal of sampling clock Sck is applied to a point H (sampling clock for ADC's) in FIG. 24. The ADC starts sampling operation at a timing of rise (arrow) of the sampling clock Sck. The system is operated as a whole by a system clock synchronized with the sampling clock Sck. At the timing of arrow, a received signal is sampled by the ADC and converted by the first waveform conversion unit (digital mixer) 16 into a signal having a baseband and a sum frequency part, the converted signal being represented by D1, D2, D3, . . . (each of which is a quantized received signal obtained by quantizing the amplitude of the received signal each time that the sampling clock signal rises and in the example of FIG. 26, a signal Di converted into a baseband and a sum frequency part has an amplitude of (m+4) bits). The converted signals are processed by the cumulation circuit 4. For example, in the case of the construction of FIG. 27, an output B of the cumulation circuit 4 takes the form of (D1+D2+D3)=R1, (D2+D3+D4)=R2 . . . , indicating that received signals Di to be added over three sampling clock signals are put together and added to deliver addition results.

Each of the output signals R1, R2, R3, . . . ,Ri, . . . of the cumulation circuit has a sum frequency part suppressed by filtering and as a result, substantially takes the form of a baseband signal. The baseband signal is stored in the temporary memory 34. It is now considered that received beams are formed in different directions at each alternate system clock signal. For example, a received beam (a beam) is formed in an a direction at an even system clock signal and a received beam (b beam) is formed in a b direction at an odd system clock signal. It is now assumed that a received signal to be added to a first received signal of a beam on a reference channel (which is, for example, the center channel of the plurality of channels constituting the receiving aperture) is R2, a next received signal on the reference channel is a first received signal for b beam, and a received signal to be added to the first received signal for b beam is R1. Here, the order of received signals used for beam formation is inverted to R2 and R1 as compared to the arrangement of the received signals delivered out of the cumulation circuit. Accordingly, the output signals from the cumulation circuit are temporarily stored in the temporary memory 34 so that for example, the received signal of R2 may be read out of the temporary memory 34 at a fourth system clock signal and the received signal of R1 may be read at the next system clock signal to ensure that the received signals necessary for received beam formation can be taken out of the temporary memory in a necessary order. Of the received signals delivered out of the temporary memory, data R2 is applied with phase compensation data aF1 for formation of a beam in a first stage of focus by means of a digital phase compensate signal generator 21. The signal processing necessary for formation of received beams in the different directions is carried out in this manner and thereafter, pieces of data Ri are sequentially delivered out of the temporary memory and added by the digital adder 3 while maintaining the order of signals of each channel and the order of con signal compensation for delay, an envelope is determined by the envelope conversion unit 28 and finally, signals of a received multibeam obtained from the DSC 29 in a time sharing fashion are displayed simultaneously as an image display on the display unit 30.

As shown in FIGS. 24 and 25, as compared to the order of output signal C of the cumulation circuit 4, the order of the output signals of the temporary memory is changed to R2, R1, R4, . . . upon delivery and R2 is applied with phase compensate data aF1 for formation of a beam in a first stage of focus by means of the digital phase compensate generator 21.

The next R1 is applied with phase compensation data bF1 for b beam of a first stage of focus. Thereafter, a second waveform conversion unit 17 performs a phase rotation processing for making the first received signal a1 of a beam, the first received signal b1 of b beam, the second received signal a2 of a beam and so on be delivered in this order. The thus delivered received signals are sequentially written in a digital delay circuit 7 such as a memory. By reading the received signals a1, b1, a2, . . . from the digital delay circuit 7 in synchronism with the delivery of received signals from the digital delay circuit of a channel used as a reference for delay time processing, a time delay can be applied. For example, in the example of FIG. 25, a delay time of two system clocks is applied to the received signal and the delivery from the digital delay circuit is such that the first received signal a1 for formation of a beam of the reference channel (second channel) is delivered at a timing of delivery of a sixth sampling clock signal, whereby in the present channel (fourth channel) set forth so far, the first received signal a1 for formation of a beam is also delivered at the timing of delivery of the sixth sampling clock signal and added with output signal a1 of the reference channel (second channel).

Accordingly, it will be seen that by making delivery from the digital delay circuit delayed by two clocks, a time delay of two clocks can be realized. Here, the focus stage is used to change focus data (data read out of the digital delay circuit (memory) and data for phase rotation) with time in order to obtain excellent focus at all focal depths by dynamically changing the focal distance and a section of the same focus data is defined as "stage". Thus, the multi-direction delay unit 27 processes the sampled received signals in a time sharing fashion and delivers received signals for formation of a received multibeam. The delivered data pieces for all channels constituting the receiving aperture are added by the digital adder 3 and then the same contents of the signal processing as above is repeated. The thus obtained signals representative of a received multibeam are temporarily stored in the digital scan converter (DSC) and are simultaneously displayed as the received multibeam on the display unit.

In an ultrasonic signal processor for performing the signal control processing and signal processing by means of a personal computer, the contents of the processing of forming a received beam and DSC processing is dealt with digitally. The sequence shown in FIG. 25 is usually subjected to timing adjustment by means of, for example, a latch because of limited circuit operation speed of LSI but for convenience of explanation of the principle, an ideal operation is illustrated.

When considering the period of formation of data for formation of one received beam, for example, data a1, a2 and a3 for a beam, it will be seen the period of data formation is two clocks of the Sck and is twice the sampling period for the ADC, indicating that the signal processing speed for formation of one received beam is of a low frequency.

Figure 28:
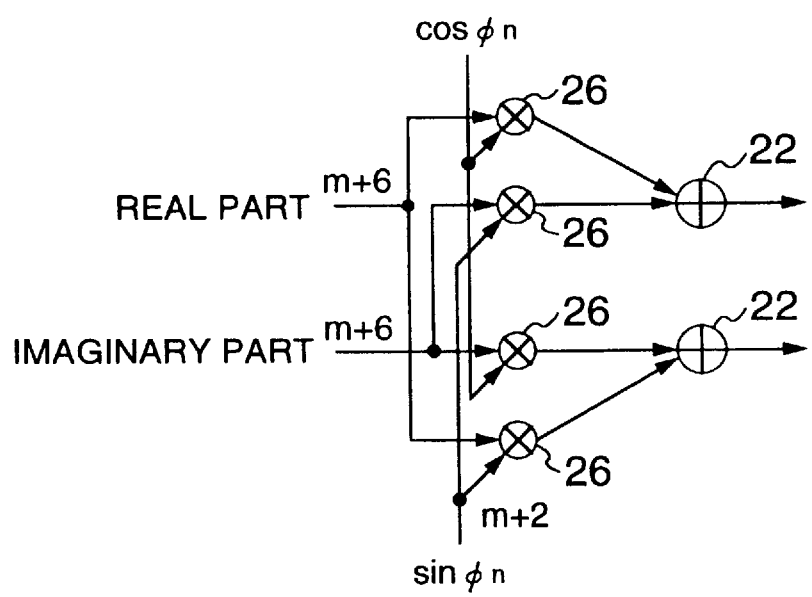
FIG. 28 is a diagram showing an example of the construction of a second waveform conversion unit.

Illustrated in FIG. 28 is an example of construction of the second waveform conversion unit 17. Each input complex signal is multiplied by a phase signal ($\cos\phi_n$, $\sin\phi_n$) having its phase rotation amount $\phi_n$ which is 90° out of phase with respect to the input signal (real part, imaginary part) by means of digital multipliers 26 and output signals of the two multipliers are added by means of a digital adder 22 to effect phase rotation. Data indicative of the phase rotation amount at that time is inputted from the digital phase compensation signal generator 21 of FIG. 24 in association with each channel. To explain with reference to FIG. 25, one received beam is dynamically focused as described previously and on the assumption that the focal position is switched each time that four sampling clock signals 5 are delivered, the focus stages are designated by F1, F2, . . .

aF1 is data of a first focus stage of a beam. The phase rotation data is aF1 at a timing of delivery of a fourth sampling clock signal, is bF1 for a first focus stage of b beam at a timing of delivery of a fifth sampling clock signal, is aF1 for the first focus stage for a beam at a timing of delivery of a sixth sampling clock signal and is bF1 for the first focus stage for b beam at a timing of delivery of a seventh sampling clock signal, and the focus position is switched at a timing of delivery of an eighth sampling clock signal to provide the phase rotation data which is aF2 for a second focus stage of a beam. In this manner, focus data used for rotation is changed and controlled.

Eleventh Embodiment

An eleventh embodiment of the present invention will now be described.

Figure 29:
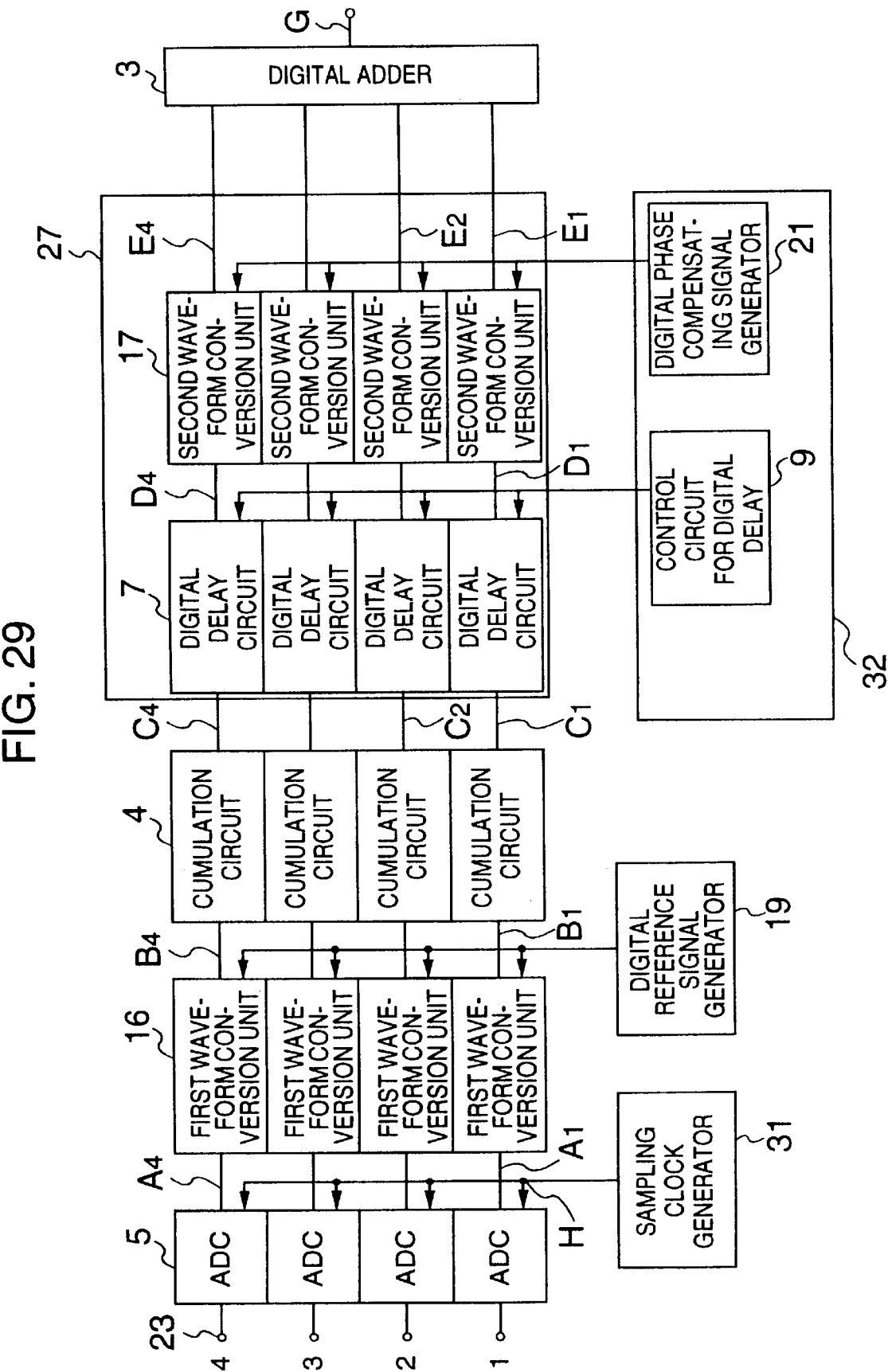
FIG. 29 is a diagram showing a construction of an essential part of an ultrasound signal processor according to an eleventh embodiment of the present invention.

Referring to FIG. 29, there is illustrated another example of construction of the multi-direction delay unit 27 in which the digital delay circuit 7 precedes the second waveform conversion unit 17. Illustrated in FIG. 35 is a sequence effected by the construction shown in FIG. 29 (symbolized similarly to FIG. 25) in which, after one ultrasonic transmission operation, a plurality of ultrasound received beams are formed from received signals generated from respective transducers forming the receiving aperture and received beams are formed in different directions. In FIG. 35, timings of output signals from the respective signal processing units are illustrated by taking a fourth channel, for instance, but the same holds true for another channel. As shown in FIG. 35, output signals of a cumulation circuit are delayed to select received signals for formation of a received multibeam and the selected received signals are delivered to the second waveform conversion unit.

Output signals R1, R2, R3, . . . , Ri, . . . of the cumulation circuit are stored in the digital delay circuit (memory) 7. When reading data from the digital delay circuit (memory) 7, a delay time from the reference channel (second channel) is compensated to form a received beam (a beam) in an a direction at an even system clock Sck and a received beam (b beam) in a b direction at an odd system clock. When a delay time of two system clocks from the reference channel (second channel) is necessary for a beam and a delay time of four system clocks from the reference channel is necessary for b beam, R2 is read with a delay time of two system clocks for a beam and R1 is read with a delay time of four system clocks for b beam as shown in FIG. 35, thus realizing a delay for each received signal. The delayed signals are multiplied by phase compensation data to perform phase compensation (phase rotation), so that results subject to highly accurate delay process are sequentially delivered. Received signals sequentially delivered out of the multi-direction delay units 27 are added together by means of the digital adder 3 while keeping unchanged the order of formation of received beams of each channel and the order of delayed received signals of each channel to be added, an envelope is determined by the envelope conversion unit 28 and finally, signals of a received multibeam generated from the DSC 29 are image-displayed simultaneously on the display unit 30. Thus, by forming a plurality of ultrasound received beams from received signals generated from the respective transducers forming the receiving aperture after one transmission operation of ultrasound, a plurality of received beams can be formed on one channel in a time sharing fashion. The above operation is repeated to scan a beam, thus obtaining an image. The timing for reading data from the digital delay circuit (memory) is controlled by a control circuit for digital delay 9.

Twelfth Embodiment

Figure 30:
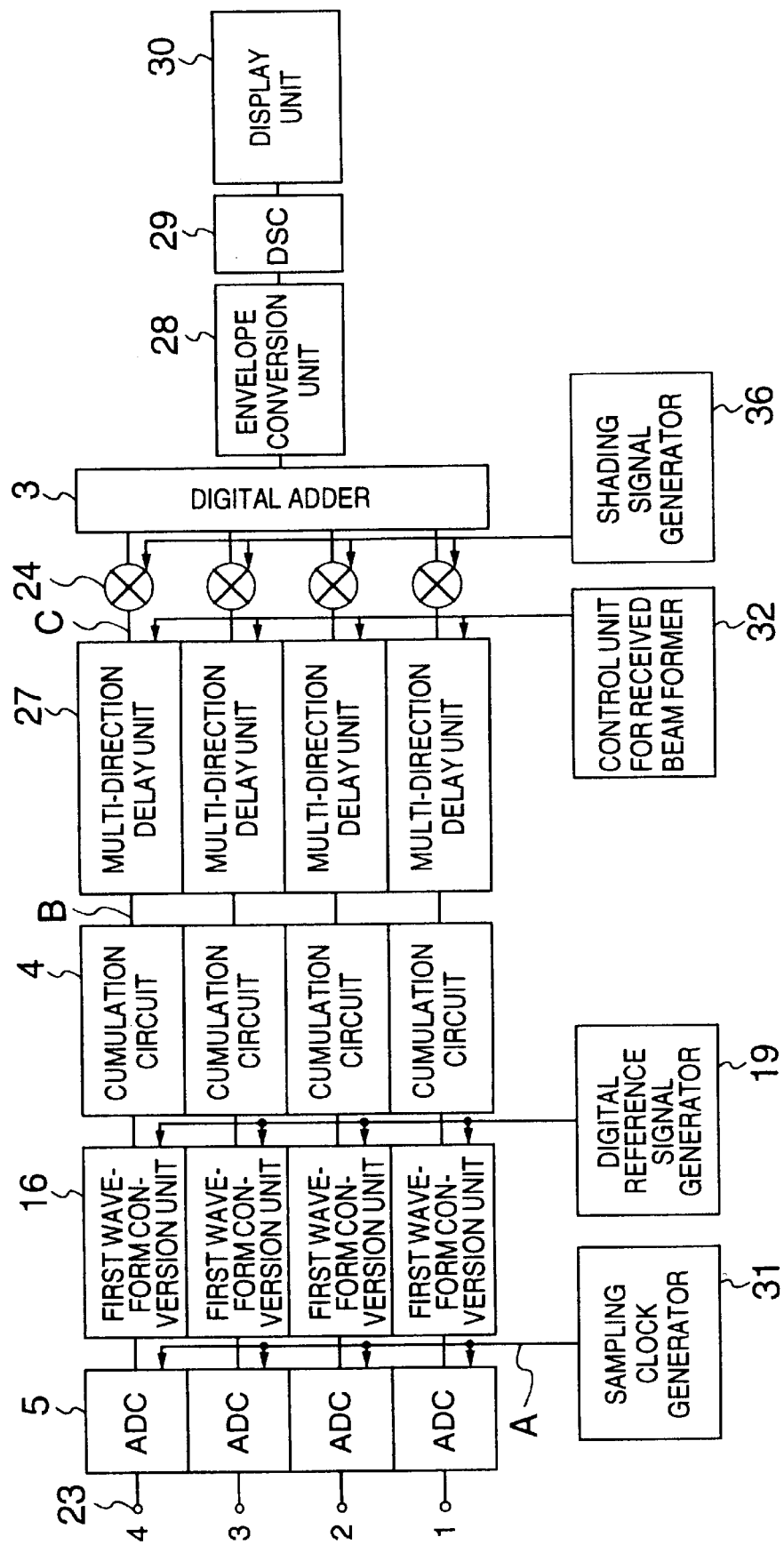
FIG. 30 is a diagram showing a construction of the essential part of an ultrasound signal processor according to a twelfth embodiment of the present invention.

A twelfth embodiment in which received signals are shaded to decrease unwanted responses of ultrasound beams is constructed as shown in FIG. 30. Digital shading networks 24 succeeding outputs of the multi-direction delay units 27 are provided on respective channels. Shading data is supplied from a shading signal generator 36 to each channel to form an excellent received beam of less unwanted response.

Thirteenth Embodiment

Figure 31:
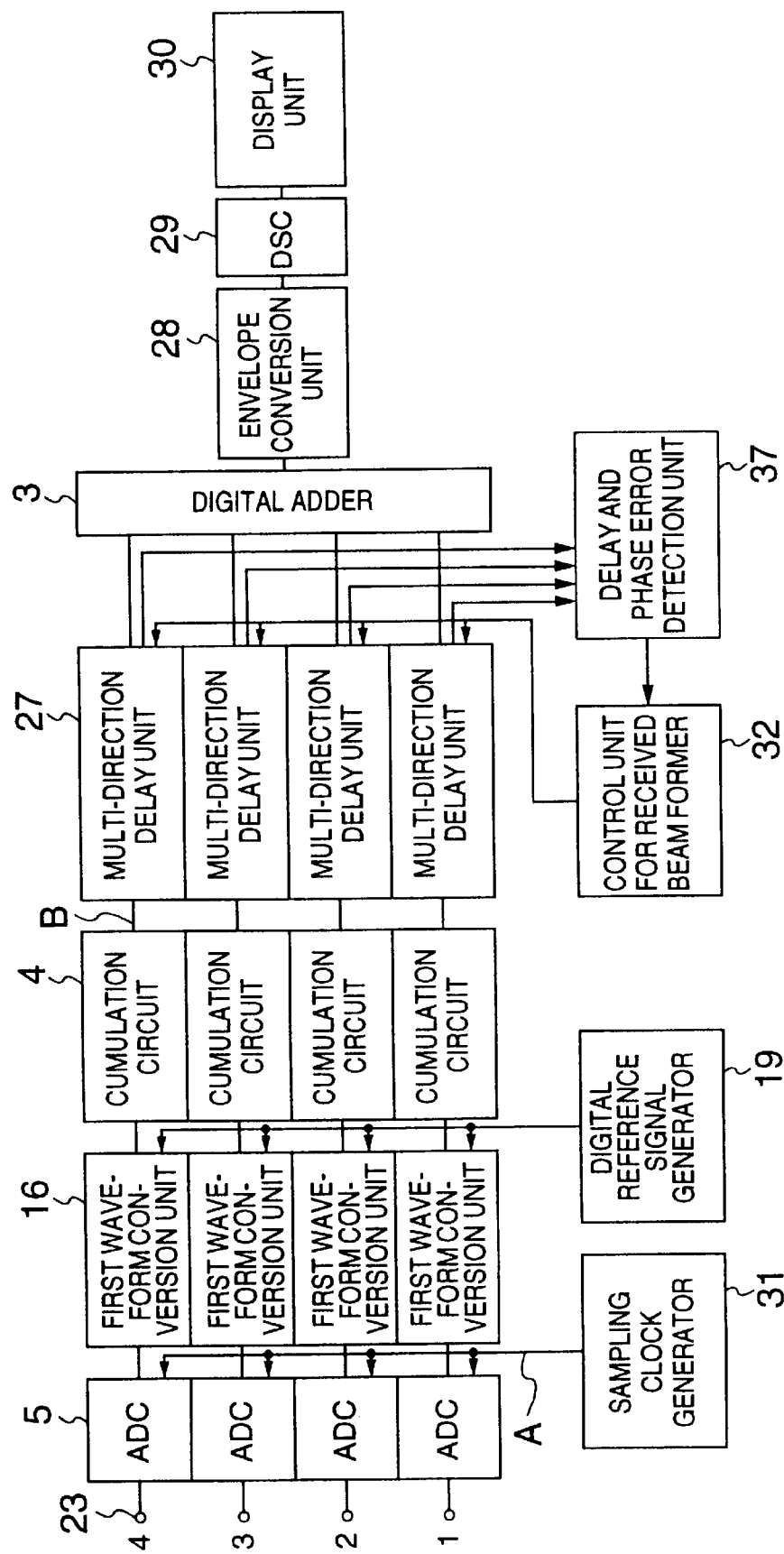
FIG. 31 is a diagram showing a construction of an essential part of an ultrasound signal processor according to a thirteenth embodiment of the present invention.

A thirteenth embodiment is constructed as shown in FIG. 31. Preset focus data becomes blurred because of irregularity in distribution of sound speeds in a living body. In the present embodiment, the focal blur is compensated by determining a phase error between adjacent channels from delayed complex received signals of the respective channels by means of a delay and phase error detection unit 37 for detecting a phase difference on the basis of phase multiplication or phase correlation and feed-backing the phase error and a time error converted therefrom to the control unit for received beam former 32 so as to modify a received beam formation controlling condition.

Fourteenth Embodiment

Figure 32:
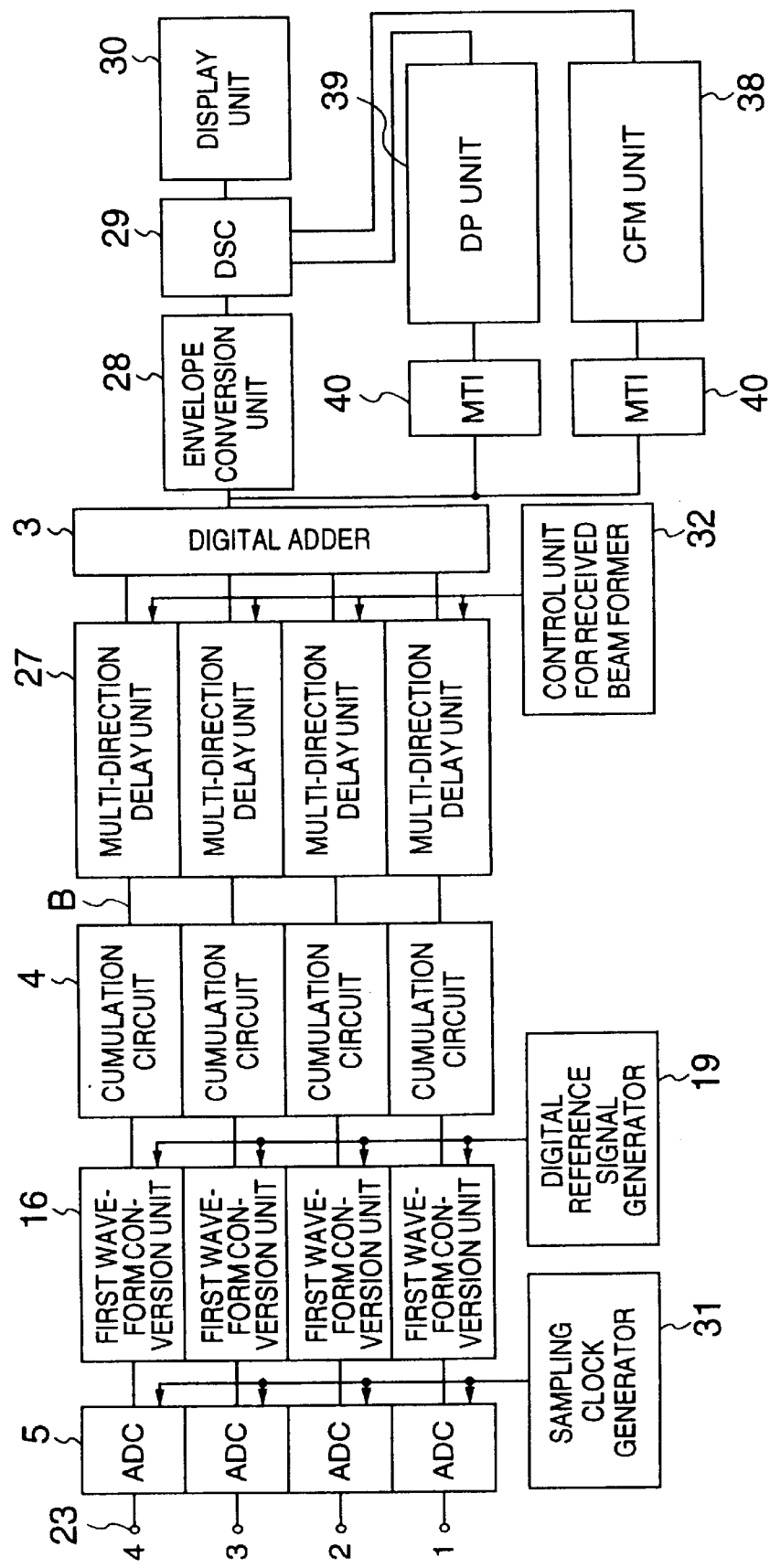
FIG. 32 is a diagram showing a construction of a fourteenth embodiment of the present invention.
Figure 33:
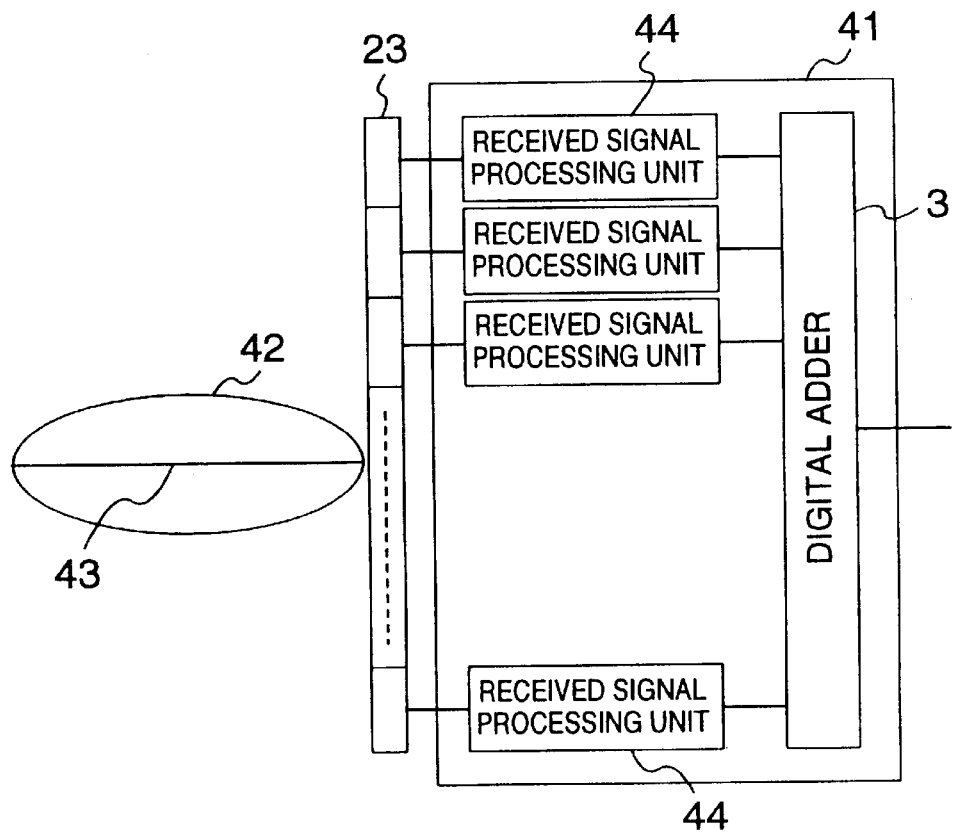
FIG. 33 is a diagram showing a construction of an essential part of a conventional ultrasound signal processor.
Figure 34:
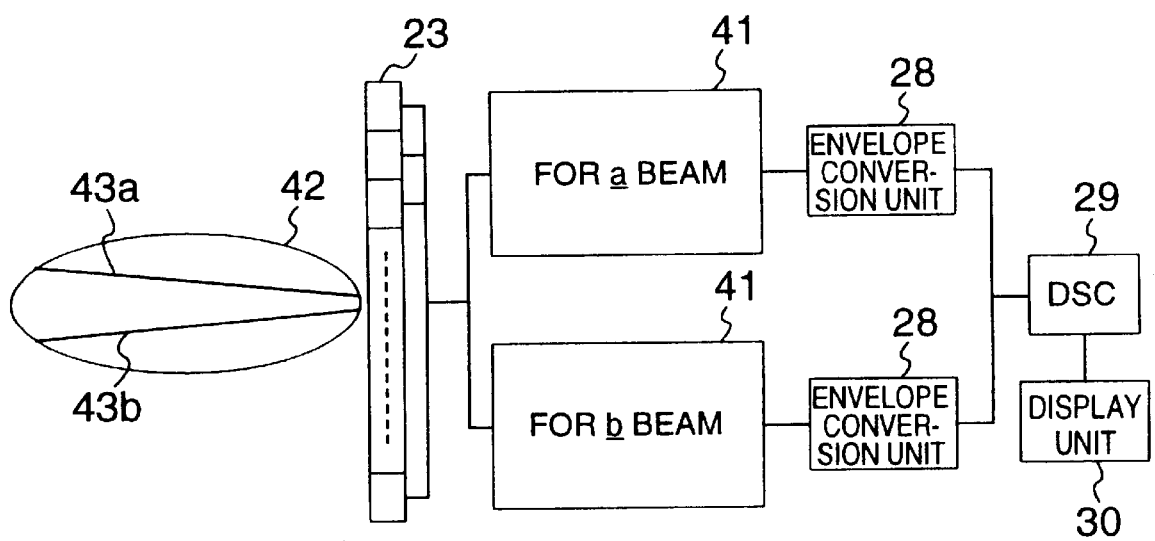
FIG. 34 is a diagram for explaining an example of a received multibeam in a conventional ultrasound signal processor.

A fourteenth embodiment is constructed as shown in FIG. 32. In the Doppler (DP) processing and the color flow mapping (CFM) processing for two-dimensional color display of blood flow, the received signal is usually lowered to a baseband and then processed. Since in the signal processing method the received signal is lowered to the baseband, the received signal is passed through a moving target indication (MTI) 40 so as to detect a blood flow by means of a CFM unit 38 and a DP unit 39. The MTI is a fixed target eliminating filter based on high-pass filtering and adapted to eliminate a low frequency component representative of an artifact of a low frequency near 0 frequency due to motion of other internal organs rather than blood flow caused by respiration and heart motion.

In the foregoing, the formation of a received multibeam has been described but when a single received beam is formed, the signal processing after the cumulation processing may be carried out using a 1/m system clock or directly using a system clock of the same rate as the sampling clock for the ADC. The speed of the signal processing after the cumulation processing can be changed by changing control data of the control unit for received beam former.

While in the foregoing embodiments the present invention has been described, for simplification of explanation, by way of sector scanning in which the received signal processing circuit (received signal channel) is connected to the transducer in one to one relation and the transmitting and receiving aperture is formed by all transducers, the present invention is in no way limited thereto. In addition to the sector scanning, the present invention can be applied to an ultrasound signal apparatus needing the function of selecting an element (transducer) for wave transmission and reception (transmitting and receiving aperture selection) by means of, for example, a linear or convex ultrasonic probe, in a similar way to that in each of the foregoing embodiments. In the present invention, so long as the number of received signal processing circuits equals the number of transducers forming the receiving aperture, the processing can be carried out in which after one transmission operation of ultrasound, a plurality of ultrasound received beams are formed from received signals generated from the respective transducers forming the receiving aperture.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and scope of the claims.

What is claimed is:

1. An ultrasound signal processor, comprising:
   a plurality of analog to digital converters each connected to a respective one of a plurality of ultrasonic transducers, each of said analog to digital converters digitizing, in a preset digitizing period, a plurality of echo signals received by said respective ultrasonic transducer which is connected to a respective one of said analog to digital converters;
   a plurality of beam forming circuits each connected to a respective one of said analog to digital converters, said beam forming circuits processing said echo signals to form signals for producing a plurality of received ultrasonic beams; and
   a digital adder which adds the output of each of said beam forming circuits;
   wherein each of said beam forming circuits comprises:
      a first waveform conversion circuit which converts, by complex signal processing, the digital signals output from said respective analog to digital converter by multiplying the digital signals output by said respective analog to digital converter by digital reference signals of preset frequencies,
      a cumulation circuit which performs, by complex signal processing, cumulation processing of the output signals from said first waveform conversion circuit in a periodic time which is longer than the preset digitizing period,
      a single multi-direction delay circuit which matches wave fronts of said echo signals received at each of said ultrasonic transducers forming a receiving aperture, and which compensates a time difference required for ultrasonic wave propagating through a distance difference between a target focus position and each of said ultrasonic transducers in terms of time or phase, and
      a control circuit which controls each of said multi-direction delay circuits;
   wherein each of said beam forming circuits processes the echo signals received by each of said ultrasonic transducers forming a receiving aperture after a single transmission ultrasonic wave, and said control circuit controls each of said multi-direction delay circuits to obtain signals for forming said plurality of received ultrasonic beams in a plurality of different directions by delaying, by a time sharing processing, output signals from each of said cumulation circuits.

2. An ultrasound signal processor according to claim 1, wherein said control circuit further comprises:
   a phase error detection circuit which detects a phase difference between outputs from said multi-direction delay circuits which receives signals output by adjacent ultrasonic transducers;
   wherein said control circuit corrects said phase difference such that a corrected phase between outputs from said multi-delay circuits, which receives signals output by the adjacent ultrasonic transducers is substantially zero.

3. An ultrasound signal processor according to claim 1, further comprising:
   a system clock which controls said ultrasound signal processor in a single periodic time which is equal to a periodic time of said system clock, the preset digitizing period being equal to said periodic time of said system clock.

4. An ultrasound signal processor, comprising:
   a plurality of analog to digital converters each connected to a respective one of a plurality of ultrasonic transducers, each of said analog to digital converters digitizing, in a preset digitizing period, a plurality of echo signals received by said respective ultrasonic transducer which is connected to a respective one of said analog to digital converters;
   a plurality of beam forming circuits each connected to a respective one of said analog to digital converters, said beam forming circuits processing said echo signals to form signals for producing a plurality of received ultrasonic beams; and
   a digital adder which adds the output of each of said beam forming circuits;
   wherein each of said beam forming circuits comprises:
      a first waveform conversion circuit which converts, in complex signal processing, the digital signals output from said respective analog to digital converter by multiplying the digital signals output by said analog to digital converter by digital reference signals of preset frequencies, a cumulation circuit which performs, by complex signal processing, cumulation processing of the output signals from said first waveform conversion circuit in a periodic time which is longer than the preset digitizing period, a single multi-direction delay circuit which includes a single temporal memory which stores output signals from said cumulation circuit, a single second waveform conversion circuit which rotates phases of signals read out from said single temporal memory, and a single digital delay circuit which delays output signals from said single second waveform conversion circuit to correct an ultrasonic wave travelling time difference produced by a difference of distances between each of said ultrasonic transducers and a position at which the ultrasonic beam has been focused, and a control circuit which controls each of said multi-direction delay circuits;

wherein each of said beam forming circuits processes the echo signals received by each of said ultrasonic transducers forming a receiving aperture after a single transmission ultrasonic wave, and said control circuit controls, in said single multi-direction delay circuit, reading out of signals from said single temporal memory by a time sharing processing, phase rotating of the signals read out from said single temporal memory by said single second waveform conversion circuit, and delaying phase rotated signals by said single second waveform conversion circuit, to obtain signals for forming said plurality of received ultrasonic beams in the time sharing processing in a plurality of different directions.

5. An ultrasound signal processor according to claim 4, wherein said control circuit further comprises:

a phase difference detecting circuit which detects a phase difference between outputs from said digital delay circuits which receives signals output by adjacent ultrasonic transducers;

wherein said control circuit further controls said temporal memories, said second waveform conversion circuits and said digital delay circuits, and corrects said phase difference such that a corrected phase between outputs from said digital delay circuits, which receives signals output by the adjacent ultrasonic transducers is substantially zero.

6. An ultrasound signal processor according to claim 4, further comprising:

a system clock which controls said ultrasound signal processor in a single periodic time which is equal to a periodic time of said system clock, the preset digitizing period being equal to said periodic time of said system clock.

7. An ultrasound signal processing, comprising:

a plurality of analog to digital converters each connected to a respective one of a plurality of ultrasonic transducers, each of said analog to digital converters digitizing, in a preset digitizing period, a plurality of echo signals received by said respective ultrasonic transducer which is connected to a respective one of said analog to digital converters;

a plurality of beam forming circuits each connected to a respective one of said analog to digital converters, said beam forming circuits processing said echo signals to form signals for producing a plurality of received ultrasonic beams; and a digital adder which adds the output of each of said beam forming circuits;

wherein each of said beam forming circuits comprises:

a first waveform conversion circuit which converts, in complex signal processing, the digital signals output from said respective analog to digital converter by multiplying the digital signals output by said respective analog to digital converter by digital reference signals of preset frequencies, a cumulation circuit which performs, by complex signal processing, cumulation processing of the output signals from said first waveform conversion circuit in a periodic time which is longer than the preset digitizing period, a single multi-direction delay circuit which includes a single digital delay circuit which delays output signals from said cumulation circuit, and a single second waveform conversion circuit which rotates phases of signals output from said single digital delay circuit, and a control circuit which controls each of said multi-direction delay circuits;

wherein each of said beam forming circuits processes the echo signals received by each of said ultrasonic transducers forming a receiving aperture after a single transmission ultrasonic wave, and said control circuit controls, in said single multi-direction delay circuit, the applying of a delay time to signals from said cumulation circuit by said single digital delay circuit by a time sharing processing, and phase rotating output signals from said single digital delay circuit, to obtain signals for forming said plurality of received ultrasonic beams in the time sharing processing in a plurality of different directions.

8. An ultrasound signal processor according to claim 7, wherein each of said beam forming circuits further comprises:

a shading circuit which shades output of said single second waveform conversion circuit.

9. An ultrasound signal processor according to claim 7, wherein said control circuit further comprises:

a phase difference detecting circuit which detects a phase difference between outputs from said second waveform conversion circuits which receives signals output by adjacent ultrasonic transducers; and a digital delay controlling circuit which controls said digital delay circuits and corrects said phase difference such that a corrected phase between outputs from said second waveform conversion circuits, which receives signals output by the adjacent ultrasonic transducers is substantially zero.

10. An ultrasound signal processor according to claim 7, further comprising:

a system clock which controls said ultrasound signal processor in a single periodic time which is equal to a periodic time of said system clock, the preset digitizing period being equal to said periodic time of said system clock.

11. An ultrasound signal processor, comprising:

a plurality of analog to digital converters each connected to a respective one of a plurality of ultrasonic transducers, each of said analog to digital converters digitizing, in a preset digitizing period, a plurality of echo signals received by said respective ultrasonic transducer being connected to said analog to digital converter;

a plurality of beam forming circuits each connected to a respective one of said analog to digital converters, said beam forming circuits processing said echo signals to form signals for producing a plurality of received ultrasonic beams; and a digital adder which adds the output of each of said beam forming circuits;

wherein each of said beam forming circuits comprises:

a first waveform conversion circuit which converts, by complex signal processing, the digital signals output from said respective analog to digital converter by multiplying the digital signals output by said respective analog to digital converter by digital reference signals of preset frequencies, a cumulation circuit which performs, by complex signal processing, cumulation processing of the output signals from said first waveform conversion circuit in a periodic time which is longer than the preset digitizing period, a single multi-direction delay circuit comprising a single memory which stores output signals from said cumulation circuit, and a signal second waveform conversion circuit which rotates phases of signals read out from said single memory, and a control circuit which controls each of said multi-direction delay circuits;

wherein each of said beam forming circuits processes the echo signals received by each of the ultrasonic transducers forming a receiving aperture after a single transmission ultrasonic wave, and said control circuit controls, in said single multi-direction delay circuit, the reading out of signals from said single memory by a time sharing processing, and phase rotating of the signals read out from said single memory by said single second waveform conversion circuit, to obtain signals for forming said plurality of received ultrasonic beam in the time sharing processing in a plurality of different directions.

12. An ultrasound signal processor according to claim 11, further comprising:

a system clock which controls said ultrasound signal processor in a single periodic time which is equal to a periodic time of said system clock, the preset digitizing period being equal to said periodic time of said system clock.

13. A method for an ultrasound signal processing, said method comprising the steps of:

(1) digitizing a plurality of echo signals received by each of a plurality of ultrasonic transducers to obtain digital echo signals, in a preset digitizing period;

(2) producing a plurality of received ultrasonic beams by processing said received echo signals by each of said ultrasonic transducers to form signals; and (3) adding results of said received ultrasonic beam forming processing for said received echo signals by each of said ultrasonic transducers;

wherein said received ultrasonic beam forming processing for said received echo signals by each of said ultrasonic transducers comprises the steps of:

(2a) obtaining first waveform signals by multiplying the digital echo signals obtained from each of said ultrasonic transducers by digital reference signals of preset frequencies, (2b) cumulating said first waveform signals in a periodic time which is longer than the preset digitizing period, and (2c) matching wave fronts of said echo signals received at each of said ultrasonic transducers forming a receiving aperture, and compensating a time difference required for ultrasonic wave propagating through a distance difference between a target focus position and each of said ultrasonic transducers in terms of time or phase;

wherein the step of (2c) is processed in a time sharing processing, and said plurality of received ultrasonic beams in a plurality of directions are formed in the time sharing processing from the echo signals received at each of the ultrasonic transducers forming a receiving aperture after a single transmission ultrasonic wave; and wherein said ultrasonic signal processing is controlled in a single periodic time which is equal to a periodic time of a system clock, and the preset digitizing period is equal to said periodic time of said system clock.

14. A method according to claim 13, wherein said received ultrasonic beam forming processing further comprises the steps of:

(2d) detecting a phase difference between results obtained from said received ultrasonic beam forming processing for adjacent ultrasonic transducers;

(2e) correcting said phase difference such that a corrected phase between results obtained from said received ultrasonic beam forming processing for the adjacent ultrasonic transducers is substantially zero.

15. A method for an ultrasound signal processing, said method comprising the steps of:

(1) digitizing a plurality of echo signals received by each of a plurality of ultrasonic transducers to obtain digital echo signals, in a preset digitizing period;

(2) producing a plurality of received ultrasonic beams by processing said received echo signals by each of said ultrasonic transducers to form signals; and (3) adding results of said received ultrasonic beam forming processing for said received echo signals by each of said ultrasonic transducers;

wherein said received ultrasonic beam forming processing for said received echo signals by each of said ultrasonic transducers comprises the steps of:

(2a) obtaining first waveform signals by multiplying the digital echo signals obtained from each of said ultrasonic transducers by digital reference signals of preset frequencies, (2b) cumulating said first waveform signals in a periodic time which is longer than the preset digitizing period, (2c) temporarily storing said cumulated signals in a temporal memory, (2d) reading out said cumulated signals from said temporal memory by time sharing processing, (2e) obtaining second waveform signals by rotating phases of signals read out from said temporal memory, and (2f) delaying said second waveform signals to correct an ultrasonic wave travelling time difference produced by a difference of distances between each of said ultrasonic transducers and a position of which the ultrasonic beam has been focused;

wherein the steps (2d), (2e), and (2f) are processed in the time sharing processing by controlling the reading out said cumulated signals from said temporal memory to form a plurality of received ultrasonic beams in a plurality of different directions by the time sharing processing, and said plurality of received ultrasonic beams are formed form the echo signals received at each of the ultrasonic transducers forming a receiving aperture after a single transmission ultrasonic wave; and wherein said ultrasound signal processing is controlled in a single periodic time which is equal to a periodic time of a system clock, and the preset digitizing period is equal to said periodic time of said system clock.

16. A method according to claim 15, wherein said received ultrasonic beam forming processing further comprises the steps of:

(2g) detecting a phase difference between said delayed signals being converted from said received signals by adjacent ultrasonic transducers; and (2h) correcting said phase difference such that a corrected phase between said delayed signals being converted from said received signals by the adjacent ultrasonic transducers is substantially zero.

17. A method for an ultrasound signal processing, said method comprising the steps of:

(1) digitizing a plurality of echo signals received by each of a plurality of ultrasonic transducers, in a preset digitizing period;

(2) producing a plurality of received ultrasonic beams by processing said received echo signals by each of said ultrasonic transducers to form signals; and (3) adding results of said received ultrasonic beam forming processing for said received echo signals by each of said ultrasonic transducers;

wherein said received ultrasonic beam forming processing comprises the steps of:

(2a) obtaining first waveform signals by multiplying the digital echo signals obtained from each of said ultrasonic transducers by digital reference signals of preset frequencies, (2b) cumulating said first waveform signals in a periodic time which is longer than the preset digitizing period, (2c) delaying said cumulated signals to correct an ultrasonic waves travelling time difference produced by a difference of distances between each of said ultrasonic transducers and a position at which the ultrasonic beam has been focused, and (2d) obtaining second waveform signals by rotating phases of said delayed signals;

wherein the steps (2c) and (2d) are processed in a time sharing processing, and said plurality of received ultrasonic beams in a plurality of different directions are formed in the time sharing processing from the echo signals received at each of the ultrasonic transducers forming a receiving aperture after a single transmission ultrasonic wave; and wherein said ultrasound signal processing is controlled in a single periodic time which is equal to a periodic time of a system clock, and the preset digitizing period is equal to said periodic time of said system clock.

18. A method according to claim 17, wherein said received ultrasonic beam forming processing further comprises the step of:

(2e) shading said second waveform signals.

19. A method according to claim 17, wherein said received ultrasonic beam forming processing further comprises the steps of:

(2f) detecting a phase difference between said second waveform signals being converted from said received signals by adjacent ultrasonic transducers; and (2g) correcting said phase difference such that a corrected phase between said second waveform signals being converted from said received signals by the adjacent ultrasonic transducers is substantially zero.

20. A method for an ultrasound signal processing, said method comprising the steps of:

(1) digitizing a plurality of echo signals received by each of a plurality of ultrasonic transducers, in a preset digitizing period;

(2) producing a plurality of received beams by processing for said received echo signals by each of said ultrasonic transducers to form signals; and (3) adding results of said received ultrasonic beam forming processing for said received echo signals by each of said ultrasonic transducers;

wherein said received ultrasonic beam forming processing comprises the steps of:

(2a) obtaining first waveform signals by multiplying the digital echo signals obtained from each of said ultrasonic transducers by digital reference signals of preset frequencies, (2b) cumulating said first waveform signals in a periodic time which is longer than the preset digitizing period, (2c) storing said cumulated signals in a memory, (2d) reading out said cumulated signals from said memory, and (2e) obtaining second waveform signals by rotating phases of signals read out of said cumulated signals;

wherein steps (2d) and (2e) are processing in a time sharing processing to correct an ultrasonic waves travelling time difference produced by a difference of distances between each of said ultrasonic transducers and a received ultrasonic beam focus position to be subjected, and said plurality of received ultrasonic beams in a plurality of different directions are formed in the time sharing processing from the echo signals received at each of the ultrasonic transducers forming a receiving aperture after a single transmission ultrasonic wave; and wherein said ultrasound signal processing is controlled in a single periodic time which is equal to a periodic time of a system clock, and the preset digitizing period is equal to said periodic time of said system clock.

21. A plurality of beam forming circuits for use in an ultrasound signal processor, each of said beam forming circuits processing digitized received signals by each of a plurality of ultrasonic transducers to form signals for producing a plurality of received ultrasonic beams, each of said beam forming circuits comprising:

a first waveform conversion circuit which converts, in complex signal processing, the waveform of the digitized received signals by said ultrasonic transducer by multiplying the digitized received signals by digital reference signals of preset frequencies;

a cumulation circuit which performs, in complex signal processing, cumulation processing of the output signals from said first waveform conversion circuit in a periodic time which is longer than the preset period of digitizing the received signals by said respective ultrasonic transducer;

a single multi-direction delay circuit which matches wave fronts of said received signals at each of said ultrasonic transducers forming a receiving aperture, and which compensates a time difference required for ultrasonic wave propagating through a distance difference between a target focus position and each of said ultrasonic transducer in term of time or phase; and a control circuit which controls each of said multi-direction delay circuits;

wherein each of said beam forming circuits processes the received signals by each of said ultrasonic transducers forming a receiving aperture after a single transmission ultrasonic wave, and said control circuit controls each of said multi-direction delay circuits to obtain signals for forming said plurality of received ultrasonic beams in a plurality of difference directions by delaying in a time sharing processing output signals from each of said cumulation circuits.

22. A plurality of beam forming circuit according to claim 21, wherein said control circuit further comprises:

a phase error detection circuit which detects a phase difference between outputs from said multi-direction delay circuits which receives signals output by adjacent ultrasonic transducers;

wherein said control circuit corrects said phase difference such that a corrected phase between outputs from said multi-delay circuits, which receives signals output by the adjacent ultrasonic transducers is substantially zero.

23. A plurality of beam forming circuits for use in an ultrasound signal processor, each of said beam forming circuits processing digitized received signals by each of a plurality of ultrasonic transducers to form signals for producing a plurality of received ultrasonic beams, each of said beam forming circuits comprising:

a first waveform conversion circuit which converts, in complex signal processing, the wave form of the digitized received signals by said ultrasonic transducer by multiplying the digitized received signals by digital reference signals of preset frequencies;

a cumulation circuit which performs, in complex signal processing, cumulation processing of the output signals from said first waveform conversion circuit in a periodic time which is longer than the preset period of digitizing the received signals by said ultrasonic transducer;

a single multi-direction delay circuit comprising a single temporal memory which stores output signals from said cumulation circuit, a single second waveform conversion circuit which rotates phases of signals read out from said single temporal memory, and a single digital delay circuit which delays output signals from said single second waveform conversion circuit to correct an ultrasonic waves travelling time difference produced by a difference of distances between each of said ultrasonic transducers and a position at which the ultrasonic beam has been focused; and a control circuit which controls each of said multi-direction delay circuits;

wherein each of said beam forming circuits processes the received signals by each of the ultrasonic transducers forming a receiving aperture after a single transmission ultrasonic wave, and said control circuit controls, in said single multi-direction delay circuit, reading out of signals from said single temporal memory in a time sharing processing, phase rotating of the signals read out from said single temporal memory by said single second waveform conversion circuit, and delaying phase rotated signals by said single second waveform conversion circuit, to obtain signals for forming said plurality of received ultrasonic beams in the time sharing processing in a plurality of difference directions.

24. A plurality of beam forming circuit according to claim 23, wherein said control circuit further comprises:

a phase difference detecting circuit which detects a phase difference between outputs from said digital delay circuits which receives signals output by adjacent ultrasonic transducers;

wherein said control circuit further controls said temporal memories, said second waveform conversion circuits and said digital delay circuits, and corrects said phase difference such that a corrected phase between outputs from said digital delay circuits which receives signals output by the adjacent ultrasonic transducers is substantially zero.

25. A plurality of beam forming circuits for use in an ultrasound signal processor, each of said beam forming circuits processing digitized received signals by each of a plurality of ultrasonic transducers to form signals for producing a plurality of received ultrasonic beams, each of said beam forming circuits comprising:

a first waveform conversion circuit which converts, in complex signal processing, the waveform of the digitized received signals by said respective ultrasonic transducer by multiplying the digitized received signals by digital reference signals of preset frequencies;

a cumulation circuit which performs, in complex signal processing, cumulation processing of the output signals from said first waveform conversion circuit in a periodic time which is longer than the preset period of digitizing the received signals by said respective ultrasonic transducer;

a single multi-direction delay circuit comprising a single digital delay circuit which delays output signals from said cumulation circuit, and a single second waveform conversion circuit which rotates phases of signals output from said single digital delay circuit; and a control circuit which controls each of said multi-direction delay circuits;

wherein each of said beam forming circuits processes the received signals by each of the ultrasonic transducers forming a receiving aperture after a single transmission ultrasonic wave, and said control circuit controls, in said single multi-direction delay circuit, applying to signals from said cumulation circuit to a delay time by said single digital delay circuit in a time sharing processing, and phase rotating output signals from said single digital delay circuit, to obtain signals for forming said plurality of received ultrasonic beams in the time sharing processing in a plurality of different directions.

26. A plurality of beam forming circuit according to claim 25, wherein each of said beam forming circuits further comprises:

a shading circuit which shades output of said single second waveform conversion circuit.

27. A plurality of beam forming circuit according to claim 25, wherein said control circuit further comprises:

a phase difference detecting circuit which detects a phase difference between outputs from said second waveform conversion circuits which receives signals output by adjacent ultrasonic transducers; and a digital delay controlling circuit which controls said digital delay circuits and corrects said phase difference such that a corrected phase between outputs from said second waveform conversion circuits, which receives signals output by the adjacent ultrasonic transducers is substantially zero.

28. A plurality of beam forming circuits for use in an ultrasound signal processor, each of said beam forming circuits processing digitized received signals by each of a plurality of ultrasonic transducers to form signals from producing a plurality of received ultrasonic beams, each of said beam forming circuits comprising:

- a first waveform conversion circuit which converts, in complex signal processing the wave form of the digitized received signals by said ultrasonic transducer by multiplying the digitized received signals by digital reference signals of preset frequencies;
- a cumulation circuit which performs, in complex signal processing, cumulation processing of the output signals from said first waveform conversion circuit in a periodic time which is longer than the preset period of digitizing the received signals by said ultrasonic transducer;
- a single multi-direction delay circuit comprising a single memory which stores output signals form said cumulation circuit, and a single second waveform conversion circuit which rotates phases of signals read out from said single memory; and
- a control circuit which controls each of said multi-direction delay circuits;

wherein each of said beam forming circuits processes the received signals by each of said ultrasonic transducers forming a receiving aperture after a single transmission ultrasonic wave, and said control circuit controls, in said single multi-direction delay circuit, reading out signals from said single memory in a time sharing processing, phase rotating of the signals read out from said single memory by said single second waveform conversion circuit, to obtain signals for forming said plurality of received ultrasonic beams in the time sharing processing in a plurality of different directions.

* * * * *